(12) United States Patent
Shahoian et al.

(10) Patent No.: US 10,045,906 B2
(45) Date of Patent: *Aug. 14, 2018

(54) SYSTEMS AND METHODS FOR HAPTIC STIMULATION

(71) Applicant: Sparq Laboratories, LLC, Tiburon, CA (US)

(72) Inventors: Erik J. Shahoian, Sonoma, CA (US); John A. McCoy, Novato, CA (US)

(73) Assignee: Sparq Laboratories, LLC, Tiburon, CA (US)

( * ) Notice: Subject to any disclaimer, the term of this patent is extended or adjusted under 35 U.S.C. 154(b) by 557 days.

This patent is subject to a terminal disclaimer.

(21) Appl. No.: 14/427,546

(22) PCT Filed: Sep. 11, 2013

(86) PCT No.: PCT/US2013/059301
§ 371 (c)(1),
(2) Date: Mar. 11, 2015

(87) PCT Pub. No.: WO2014/043263
PCT Pub. Date: Mar. 20, 2014

(65) Prior Publication Data
US 2015/0245978 A1    Sep. 3, 2015

Related U.S. Application Data

(60) Provisional application No. 61/699,368, filed on Sep. 11, 2012, provisional application No. 61/717,829, filed on Oct. 24, 2012.

(51) Int. Cl.
*A61H 19/00* (2006.01)
*A61H 23/02* (2006.01)
(Continued)

(52) U.S. Cl.
CPC .............. *A61H 23/02* (2013.01); *A61F 5/41* (2013.01); *A61H 9/0078* (2013.01); *A61H 19/30* (2013.01);
(Continued)

(58) Field of Classification Search
CPC ........ A61H 19/00; A61H 19/30; A61H 19/32; A61H 19/34; A61H 19/40; A61H 19/44
(Continued)

(56) References Cited

U.S. PATENT DOCUMENTS 2,781,041 A    2/1957  Weinberg
4,102,335 A    7/1978  Woodward et al.
(Continued)

FOREIGN PATENT DOCUMENTS

EP    1945123 A1    7/2008
EP    2777679 A1    9/2014
(Continued)

OTHER PUBLICATIONS

3M; Scotch® Electrical Semi-Conducting Tape 13 (Datasheet); 4 pgs.; Sep. 2012; retrieved from the internet Aug. 18, 2014 from: http://multimedia.3m.com/mws/mediawebserver?mwsId=SSSSSuH8gc7nZxtUNx_Um8TSevUqe17zHvTSevTSeSSSSSS--&fn=78-8141-5624-2_R1.pdf.

*Primary Examiner* — Samuel Gilbert
(74) *Attorney, Agent, or Firm* — Shay Glenn LLP

(57) ABSTRACT

A system for sexual stimulation includes a first sexual stimulation device having a first sensor and a first actuator and a second sexual stimulation device having a second sensor and a second actuator. The first sexual stimulation device is configured to communicate information from the first sensor to actuate the second actuator of the second sexual stimulation device and the second sexual stimulation device is configured to communicate information from the second sensor to actuate the first actuator of the first sexual stimulation device.

20 Claims, 22 Drawing Sheets

(51) Int. Cl.
  *A61F 5/41* (2006.01)
  *A61H 9/00* (2006.01)
  *A61H 15/00* (2006.01)

(52) U.S. Cl.
  CPC ............ *A61H 19/32* (2013.01); *A61H 19/40* (2013.01); *A61H 19/44* (2013.01); *A61H 23/0263* (2013.01); *A61F 2005/415* (2013.01); *A61H 2015/0028* (2013.01); *A61H 2201/0192* (2013.01); *A61H 2201/1215* (2013.01); *A61H 2201/1238* (2013.01); *A61H 2201/149* (2013.01); *A61H 2201/1664* (2013.01); *A61H 2201/5005* (2013.01); *A61H 2201/5012* (2013.01); *A61H 2201/5015* (2013.01); *A61H 2201/5043* (2013.01); *A61H 2201/5058* (2013.01); *A61H 2201/5064* (2013.01); *A61H 2201/5069* (2013.01); *A61H 2201/5071* (2013.01); *A61H 2201/5079* (2013.01); *A61H 2201/5084* (2013.01); *A61H 2230/045* (2013.01); *A61H 2230/065* (2013.01); *A61H 2230/208* (2013.01); *A61H 2230/255* (2013.01); *A61H 2230/425* (2013.01); *A61H 2230/505* (2013.01); *A61H 2230/605* (2013.01)

(58) Field of Classification Search
  USPC ..................................................... 600/38–41
  See application file for complete search history.

(56) References Cited

U.S. PATENT DOCUMENTS

| | | | |
|---|---|---|---|
| 4,407,275 | A | 10/1983 | Schroeder |
| 5,331,974 | A | 7/1994 | Sook |
| 5,501,650 | A | 3/1996 | Gellert |
| 5,836,865 | A | 11/1998 | Ritchie et al. |
| 5,889,672 | A | 3/1999 | Schuler et al. |
| 5,956,484 | A | 9/1999 | Rosenberg et al. |
| 6,028,531 | A | 2/2000 | Wanderlich |
| 6,113,532 | A | 9/2000 | Yap |
| 6,179,797 | B1 | 1/2001 | Brotz |
| 6,275,213 | B1 | 8/2001 | Tremblay et al. |
| 6,336,907 | B1 | 1/2002 | Dono et al. |
| 6,368,268 | B1 | 4/2002 | Sandvick et al. |
| 6,423,017 | B2 | 7/2002 | Brotz |
| 6,551,450 | B1 | 4/2003 | Thomas et al. |
| 6,569,083 | B1 | 5/2003 | Kassman |
| 6,592,516 | B2 | 7/2003 | Lee |
| 6,651,668 | B1 | 11/2003 | Praml |
| 6,658,325 | B2 | 12/2003 | Zweig |
| 6,741,895 | B1 | 5/2004 | Gafni et al. |
| 6,793,619 | B1 | 9/2004 | Blumental |
| 6,890,293 | B2 | 5/2005 | Kobayashi |
| 7,044,924 | B1 | 5/2006 | Roth et al. |
| 7,046,151 | B2 | 5/2006 | Dundon |
| 7,096,090 | B1 | 8/2006 | Zweig |
| 7,174,238 | B1 | 2/2007 | Zweig |
| 7,438,681 | B2 | 10/2008 | Kobashikawa et al. |
| 7,577,476 | B2 | 8/2009 | Hochman et al. |
| 7,608,037 | B2 | 10/2009 | Levy |
| 7,720,572 | B2 | 5/2010 | Ziegler et al. |
| 7,762,945 | B2 | 7/2010 | Blumenthal |
| 7,812,820 | B2 | 10/2010 | Schuler et al. |
| 7,846,114 | B2 | 12/2010 | Webster et al. |
| 7,938,789 | B2 | 5/2011 | Imboden et al. |
| 8,012,082 | B1 | 9/2011 | Lefew |
| 8,016,778 | B2 | 9/2011 | Brown et al. |
| 8,255,299 | B2 | 8/2012 | Cambridge |
| 8,308,631 | B2 | 11/2012 | Kobashikawa et al. |
| 8,378,794 | B2 | 2/2013 | Alarcon |
| 8,382,656 | B1 | 2/2013 | Brown |
| 8,409,120 | B2 | 4/2013 | Knyrim |
| 8,419,611 | B1 | 4/2013 | Hatami |
| 8,449,451 | B2 | 5/2013 | Dawe |
| 8,505,086 | B2 | 8/2013 | Norman et al. |
| 8,508,469 | B1 | 8/2013 | Rosenberg et al. |
| 8,734,323 | B2 | 5/2014 | Staffolani |
| 8,751,044 | B2 | 6/2014 | Eriksson |
| 8,753,300 | B2 | 6/2014 | Deshpande |
| 8,758,282 | B2 | 6/2014 | Malhi et al. |
| 8,813,198 | B2 | 8/2014 | Louboutin et al. |
| 8,936,544 | B2 * | 1/2015 | Shahoian ............... A61H 19/30 600/38 |
| 8,994,800 | B2 | 3/2015 | Brockway et al. |
| 2002/0065477 | A1 | 5/2002 | Boyd et al. |
| 2002/0133103 | A1 | 9/2002 | Williams et al. |
| 2003/0009119 | A1 | 1/2003 | Kamm et al. |
| 2003/0036678 | A1 | 2/2003 | Abbassi |
| 2003/0083544 | A1 | 5/2003 | Richards et al. |
| 2003/0195441 | A1 | 10/2003 | Firouzgar |
| 2004/0097852 | A1 | 5/2004 | Boyd et al. |
| 2004/0132439 | A1 | 7/2004 | Tyagi et al. |
| 2005/0049453 | A1 | 3/2005 | Faulkner |
| 2006/0095158 | A1 | 5/2006 | Lee et al. |
| 2006/0247682 | A1 | 11/2006 | Gerber et al. |
| 2007/0055188 | A1 | 3/2007 | Avni et al. |
| 2007/0123748 | A1 | 5/2007 | Meglan |
| 2007/0126593 | A1 | 6/2007 | Nan |
| 2007/0150104 | A1 | 6/2007 | Jang et al. |
| 2008/0139080 | A1 | 6/2008 | Zheng |
| 2008/0299869 | A1 | 12/2008 | Hsu |
| 2009/0099413 | A1 * | 4/2009 | Kobashikawa ........ A61H 19/34 600/38 |
| 2010/0041944 | A1 | 2/2010 | Levy |
| 2010/0174137 | A1 | 7/2010 | Shim |
| 2010/0174217 | A1 | 7/2010 | Budnik et al. |
| 2010/0191048 | A1 | 7/2010 | Kulikov |
| 2011/0087337 | A1 | 4/2011 | Forsell |
| 2011/0218395 | A1 | 9/2011 | Stout |
| 2011/0245743 | A1 | 10/2011 | Eddy |
| 2012/0215141 | A1 | 8/2012 | Peddicord |
| 2012/0215189 | A1 | 8/2012 | Wu |
| 2012/0232335 | A1 | 9/2012 | Eisenberg et al. |
| 2012/0256864 | A1 | 10/2012 | Miki |
| 2012/0259171 | A1 | 10/2012 | Shmakov |
| 2012/0293435 | A1 | 11/2012 | Miki |
| 2012/0316481 | A1 | 12/2012 | Purdy et al. |
| 2013/0090524 | A1 | 4/2013 | McNamara |
| 2013/0222280 | A1 | 8/2013 | Sheynblat et al. |
| 2013/0226050 | A1 | 8/2013 | Lee |
| 2013/0331745 | A1 | 12/2013 | Sedic |
| 2014/0107542 | A1 | 4/2014 | Schubert et al. |
| 2014/0171734 | A1 | 6/2014 | Kassman |
| 2014/0207032 | A1 | 7/2014 | Dematio et al. |
| 2014/0207280 | A1 | 7/2014 | Duffley et al. |
| 2014/0235938 | A1 | 8/2014 | Schnurr |
| 2014/0243591 | A1 | 8/2014 | Weller |
| 2014/0366105 | A1 | 12/2014 | Bradley et al. |

FOREIGN PATENT DOCUMENTS

| | | |
|---|---|---|
| EP | 2777680 A1 | 9/2014 |
| EP | 2842360 A1 | 3/2015 |
| EP | 2863859 A1 | 4/2015 |
| FR | 2942713 A1 | 9/2010 |
| JP | 2006-149566 | 6/2006 |
| WO | WO98/14147 A1 | 4/1998 |
| WO | WO99/37267 A1 | 7/1999 |
| WO | WO00/15172 A1 | 3/2000 |
| WO | WO2007/033333 A1 | 3/2007 |
| WO | WO2007/047169 A2 | 4/2007 |
| WO | WO2009/048376 A1 | 4/2009 |
| WO | WO2010/032162 A1 | 3/2010 |
| WO | WO2012/101289 A1 | 8/2012 |
| WO | WO2013/175473 A1 | 11/2013 |
| WO | WO2014/138504 A2 | 9/2014 |

* cited by examiner

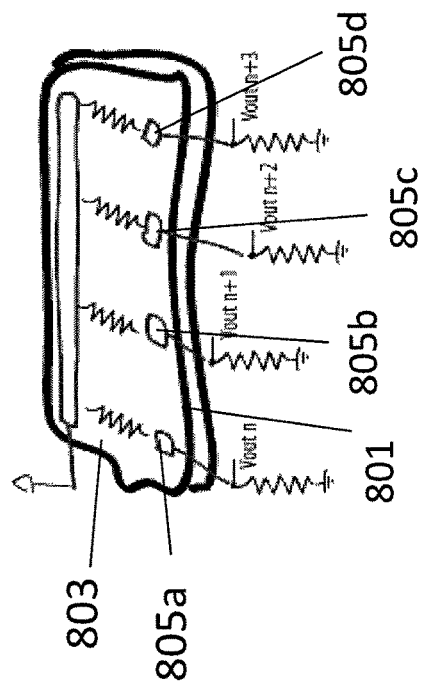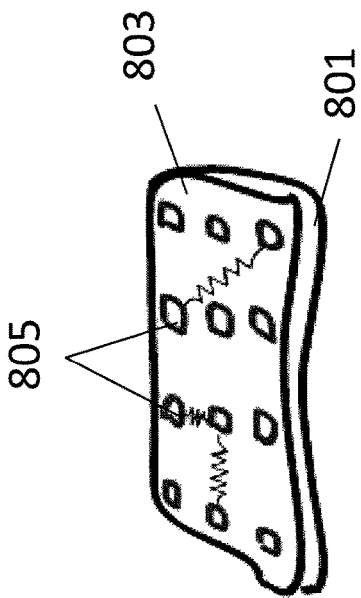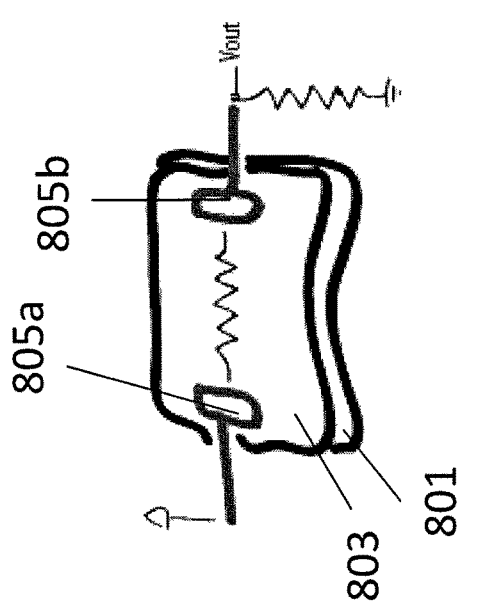
Figure 8B
Figure 8c
Figure 8A

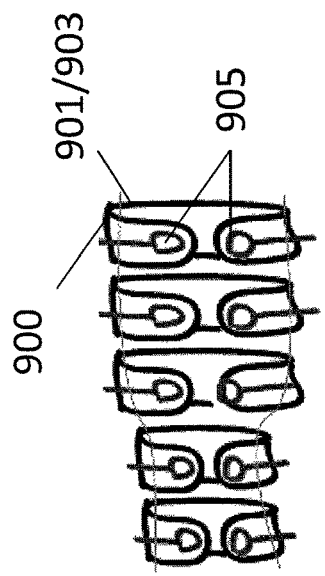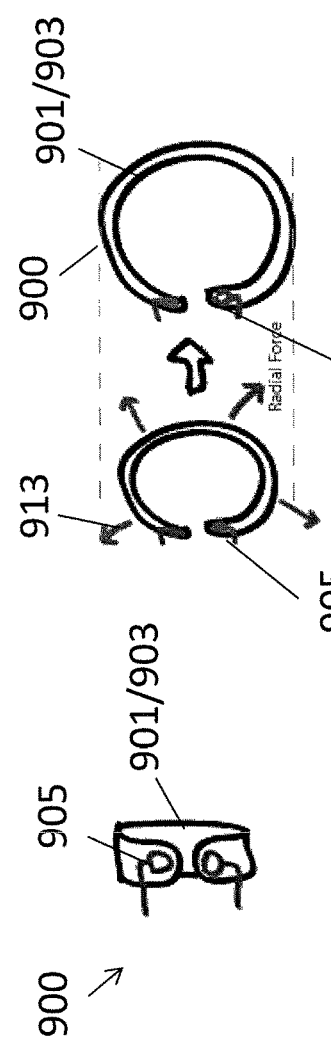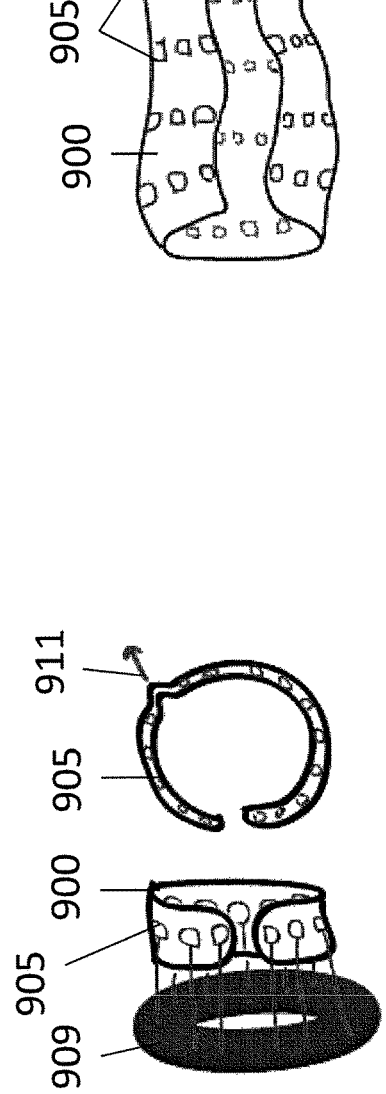

SYSTEMS AND METHODS FOR HAPTIC STIMULATION

CROSS REFERENCE TO RELATED APPLICATIONS

This application claims priority to U.S. Provisional Application No. 61/699,368, titled "SENSORS FOR REMOTE TELE-OPERATED HAPTIC INTERFACE," filed Sep. 11, 2012, and U.S. Provisional Application No. 61/717,829, titled "NETWORK FOR REMOTE TELE-OPERATED HAPTIC INTERFACE," filed Oct. 24, 2012, both of which are incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Haptic technology is the translation of the sense of touch through technology by applying forces or vibrations to a portion of a user's body. Haptic technology is currently used in a limited fashion in user input devices, such as touch screens, keyboards, computer mice, and joysticks. Basic haptic feedback can be purely mechanical, such as a clicking sensation experienced when a mouse button is depressed with sufficient force. Other devices can be configured to output haptic feedback through the use of electro-mechanical means, such as by activating and/or deactivating one or more motors. For instance, a vibratory sensation can be imparted to an input device by turning an electric motor on and off. Haptic feedback has also been incorporated in video gaming applications, such as where an actuator can output a tactile sensation based on the occurrence of an event, such as in response to a command signal from a game console.

When referring to teleoperation with sex toys, the term "teledildonics" is sometimes used. In short, teledildonics relies on real-time exchange of sensor signals, similar to haptics and tele-operation as performed in the field of robotics as early as the 1950s for military applications like diffusing bombs, or for modern remote surgery.

Sexual stimulation devices (or sex toys) are becoming more accepted by society. However, many sexual stimulated device remain unsophisticated relative to current robotic standards. While in robotics, closed-loop control systems built around sensors and actuators are common, current sexual stimulation devices tend to use very little if any actuators, sensors, or closed-loop control systems. Accordingly, a sexual stimulation device or system that includes more advanced control systems, such as haptic feedback and teledildonics, is desired.

SUMMARY OF THE DISCLOSURE

In general, in one embodiment, a device for sexual stimulation includes a sleeve having a longitudinal axis extending from a proximal end of the sleeve to a distal end of the sleeve and a ring configured to translate over the sleeve along the longitudinal axis. The ring is configured to change in diameter to vary an amount of constriction placed on the sleeve. This and other embodiments can include one or more of the following features. The device can further include a first actuator and a second actuator. The first actuator can be configured to control the translation of the ring over the sleeve, and the second actuator can be configured to control the constriction of the ring. The device can further include a drive cable connected to the first actuator and the ring can be configured to translate along the drive cable. The device can further include a controller. The controller can be configured to control the translation of the ring, such as based upon position input from a paired device. The ring can be configured to have a diameter of approximately 40-80 mm when unconstricted around the sleeve and a diameter of approximately 10-40 mm when fully constricted around the sleeve. The device can further include a controller. The controller can be configured to control the constriction of the ring. The controller can be configured to control the constriction of the ring based upon pressure input from a paired device. The device can further include a position sensor coupled to the ring. The position sensor can be configured to detect a position of the device relative to a user. The position sensor can be an accelerometer. The device can further include a communication element that can be configured to communicate the detected position to a paired device. The position sensor can be an accelerometer. The device can further include a user control that can be configured to adjust constriction of the ring or a position of the ring along the sleeve. The ring can include a telescoping portion or a coiled portion to provide for the change in diameter. The device sleeve can include an outer layer configured to engage with the ring, and the outer surface can have a coefficient of friction of less than 0.1. The sleeve can further include an inner layer comprising an oil gel material or silicone rubber. The device sleeve can further include an inner layer having a durometer of between 5 and 40 shoreA. The sleeve can be pliable.

In general, in one embodiment, a device for sexual stimulation includes an elongate body having a longitudinal axis extending from a proximal end of the sleeve to a distal end of the sleeve and an expandable ring configured to translate along the longitudinal axis. The expandable ring is configured to change diameter to expand beyond a diameter of the elongate body. This and other embodiments can include one or more of the following features. The device can further include a vibrating element positioned at an angle relative to the elongate body. The longitudinal axis of the elongate body can be curved. The device can further include a controller. The controller can be configured to control the translation of the expandable ring, such as based upon position input from a paired device. The device can further include a controller that can be configured to control the inflation of the ring. The device can further include a handle attached to the elongate body. The handle can include an inflation pump configured to inflate the expandable ring. An angular position of the elongate body relative to the handle can be adjustable. The handle can include a user control configured to adjust inflation of the expandable ring, an angular position of the elongate body relative to the handle, or a position of the ring along the elongate body. The device can further include a position sensor coupled to the expandable ring. The position sensor can be configured to detect a position of the device relative to a user. The position sensor can be an accelerometer. The device can further include a communication element configured to communicate the detected position to a paired device. The device can further include a pressure sensor configured to detect a pressure of the expandable ring. The device can further include a communication element configured to communicate the detected pressure to a paired device. The device can further include an op-amp differentiator circuit stage configured to amplify and differentiate the detected pressure of the expandable ring. The elongate body can include a semi-rigid elongate shaft. The device can further include a lead screw or cable drive within the semi-rigid elongate shaft. The lead screw or cable drive can be configured to provide translation of the expandable ring. The device can further include a sleeve over the elongate body. The ring can be configured to translate in a space between the elongate body and the sleeve. The device can further include a sleeve over the elongate body and a lubricant between the sleeve and the elongate body. The elongate body can be rigid. The expandable ring can be configured to inflate to change diameter.

In general, in one embodiment, a system for sexual stimulation includes a first sexual stimulation device having a sensor thereon and a second sexual stimulation device having a controller and an actuator. The first sexual stimulation device is configured to communicate information from the sensor to the second sexual stimulation device through an encoded audio signal. The controller is configured to decode the encoded audio signal to actuate the actuator. This and other embodiments can include one or more of the following features. The first sexual stimulation device can include a first element movable relative to a first elongate body. The second sexual stimulation device can include a second element movable relative to a second elongate body. The sensor can be configured to measure a position of the first sexual stimulator device relative to a user. The actuator can be configured to move the second movable element relative to the second elongate body based upon the measured position of the first sexual stimulator device. The first sexual stimulation device can include a second actuator and a second controller. The second sexual stimulation device can include a second sensor. The second sexual stimulation device can be configured to communicate information from the second sensor to the first sexual stimulation device through a second encoded audio signal. The second controller can be configured to decode the second encoded audio signal to actuate the second actuator. The first encoded audio signal and the second encoded audio signal can be configured to be transmitted on different frequencies. The second stimulation device can include a ring and an elongate the body. The actuator can be configured to change the diameter of the ring based upon a pressure reading from the sensor. The controller can include an embedded processor which can be configured to run a position control loop or velocity control loop to control the second sexual stimulation device based upon input from the sensor. The sensor can be an optical, magnetic, or resistive sensor. The controller can be constructed of only analog components.

In general, in one embodiment, a method of communicating between paired sexual stimulation devices includes measuring a position of a first sexual stimulation device relative to a first user, sending an encoded audio signal from the first sexual stimulation device to a second sexual stimulation device through an encoded audio signal, and actuating a sexual stimulation element of the second sexual stimulation device based upon the encoded audio signal. This and other embodiments can include one or more of the following features. The method can further include measuring a position of the second sexual stimulation device relative to a second user, sending an audio signal from the second sexual stimulation device to the first sexual stimulation device and actuating the sexual stimulation element of the first sexual stimulation device based upon the encoded audio signal from the second sexual stimulation device.

In general, in one embodiment, a device for sexual stimulation includes an elongate member having a central axis extending therethrough and a stimulation element configured to change in diameter and travel along the central axis. The device is configured to receive a communication signal from a paired device and to change the diameter or position of the stimulation element based upon the communication signal. This and other embodiments can include one or more of the following features. The device can further include a sensor configured to measure the position of the device relative to a user. The device can further be configured to send a communication signal to the paired device to communicate the measured position. The communication signal can be an encoded audio signal.

In general, in one embodiment, a system for sexual stimulation includes a first sexual stimulation device having a first sensor and a first actuator and a second sexual stimulation device having a second sensor and a second actuator. The first sexual stimulation device is configured to communicate information from the first sensor to actuate the second actuator of the second sexual stimulation device and the second sexual stimulation device is configured to communicate information from the second sensor to actuate the first actuator of the first sexual stimulation device. This and other embodiments can include one or more of the following features. The first and second sexual stimulation devices can be configured to communicate through an encoded audio signal. The first sexual stimulation device can include a first element movable relative to a first elongate body. The second sexual stimulation device can include a second element movable relative to a second elongate body. The first actuator can be configured to move the first element relative to the first elongate body, and the second actuator can be configured to move the second element relative to the second elongate body.

In general, in one embodiment, the carrier modulation channel between two devices can be subdivided into sections to enable control of several actuators in a paired device.

In general, in one embodiment, a device for sexual stimulation includes an elongate member having a central axis extending therethrough and a pliable laminate sensor located along the elongate member. The pliable laminate sensor has a plurality of electrodes thereon to measure a strain on the elongate member at a plurality of locations. The laminate sensor can include an elastomer.

In general, in one embodiment, a server can broadcast teledildonics from one sexual stimulation device to another. This and other embodiments can include one or more of the following features. Teledildonic mappings can be negotiated by the server and firmware. Teledildonics mapping can be done on the device. Teledildonics mapping can be done on a local host. Teledildonics mapping can be done on a server. There can be mixed mappings. The teledildonics can include sexual pleasure signals. Real-time sensor signals can be reduced into a parametric representation. Sexual pleasure signals can be used for teledildonic gaming. Anonymous data can be monitored for correlation of physical signals and sexual pleasure signals in order to seek optimal input over large user space. Anonymous data can be monitored for calibrated physical, in order to seek population means.

In general, in one embodiment, a method for sensing strain caused by forces between a device (sex toy or medical instrument) and anatomy, includes using one or more force sensitive resistors formed from semi-conductive materials to sense strain. This and other embodiments can include one or more of the following features. A microprocessor can act on stored sensor calibration data. The microprocessor can determine part or all of a sensor calibration or configuration. The microprocessor can scale sensor data to a normalized range. Sensing the strain can include multiplexing more than two pairs of electrodes to measure multiple strain signals. Sensing the strain can include combining multiple sensor signals to infer shape over a given area. Sensing the strain can include combining multiple sensor signals when sensors are in a known configuration in order to measure position of the device with respect to anatomy, or vice versa. Sensing the strain can include combining multiple sensor signals when sensors are in a known configuration in order to measure velocity of the device with respect to anatomy, or vice versa. Sensing the strain can include combining multiple sensor signals when sensors are in a known configuration in order to measure stroke length of the device with respect to anatomy, or vice versa. Sensing the strain can include combining multiple sensor signals when sensors are in a known configuration in order to measure stroke frequency of the device with respect to anatomy, or vice versa. The method can further include arranging sensors to measure force between the device and the anatomy. The method can further include arranging sensors to measure girth (diameter) of penis, vaginal canal, or other anatomy. The method can further include arranging sensors to measure temperature of the anatomy. The method can further include arranging sensors to measure moisture on the anatomy. The method can further include incorporating a microprocessor to compress sensor signals into parameterized form, such as for but not limited to recording, distribution, or local application. The method can further include using electrodes across the thickness of a viscoelastic material such as semi-conductive strain gauge, in order to measure forces that cause a compressive strain on the material.

In general, in one embodiment, an assembly includes a lamination of elastic semi-conductive material and other elastic materials forming a sealed sensor assembly, where the assembly is designed with compliance (designed to stretch) in one or many axes. The assembly has one or more electrical resistive connections suitable to measure that stretch electronically. This and other embodiments can include one or more of the following features. The assembly can further include capacitive connections for monitoring thickness as material deforms.

In general, in one embodiment, a method of forming an elastic variable resistor includes applying semi-conductive paint, ink, or other coating on a flexible substrate, where the substrate is part of a flexible portion of a sex toy. This and other embodiments can include one or more of the following features. Highly electrically conductive inks or coatings can be used to create conductive surfaces (plated electrodes) which are opposed to each other with elastomer between said electrodes. Capacitive measurement circuitry can be formed by flexible material and electrodes. Local deformation of material can result in changing gap between electrodes.

In general, in one embodiment, a method of forming low-resistance flexible leads to a sensor can include using conductive paint, ink, or other coating. This and other embodiments can include one or more of the following features. The electrodes can be fine conductive wires or semi-conductive thread materials molded into rubber or laminated.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 8A-8C show exemplary sensors.

FIGS. 9A-9E show exemplary ring sensors.

DETAILED DESCRIPTION

Figure 1A:
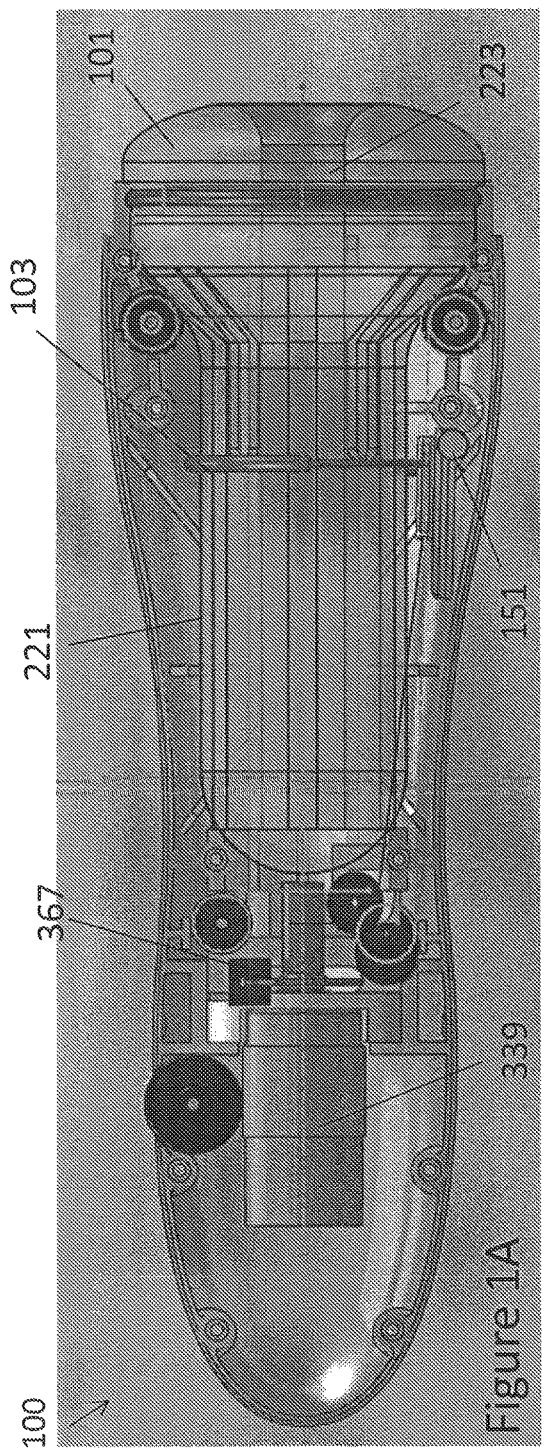
FIGS. 1A and 1B show transparent views of an embodiment of a device for sexual stimulation.
Figure 1B:
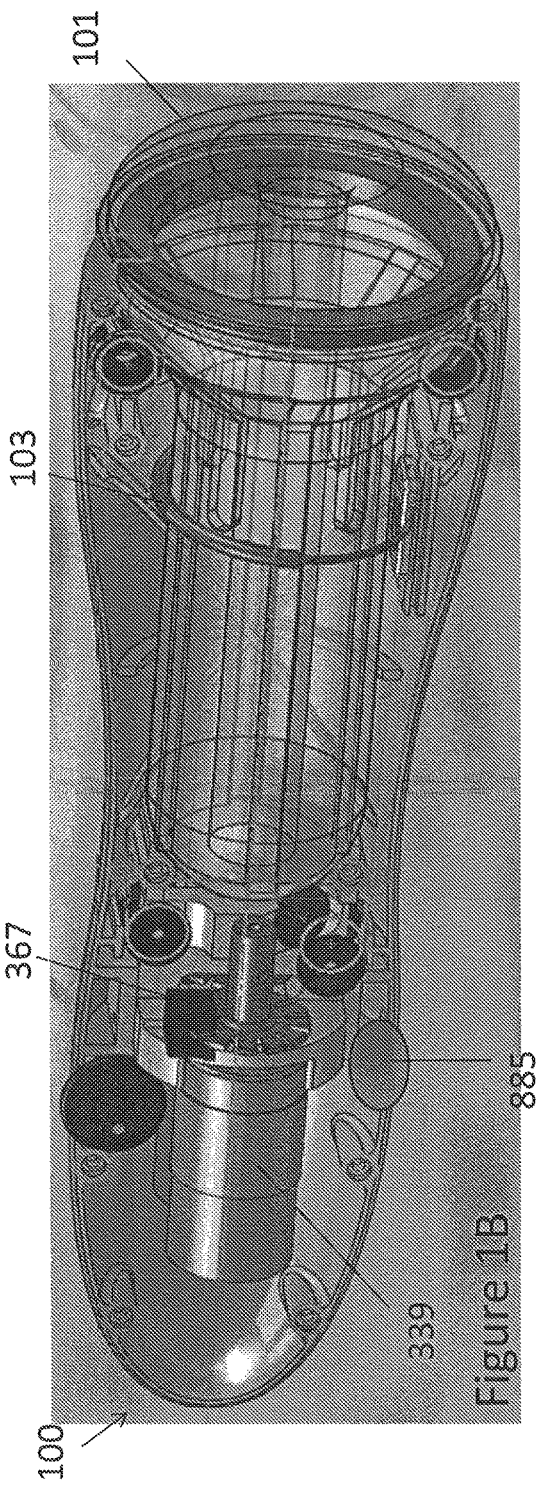
Figure 2:
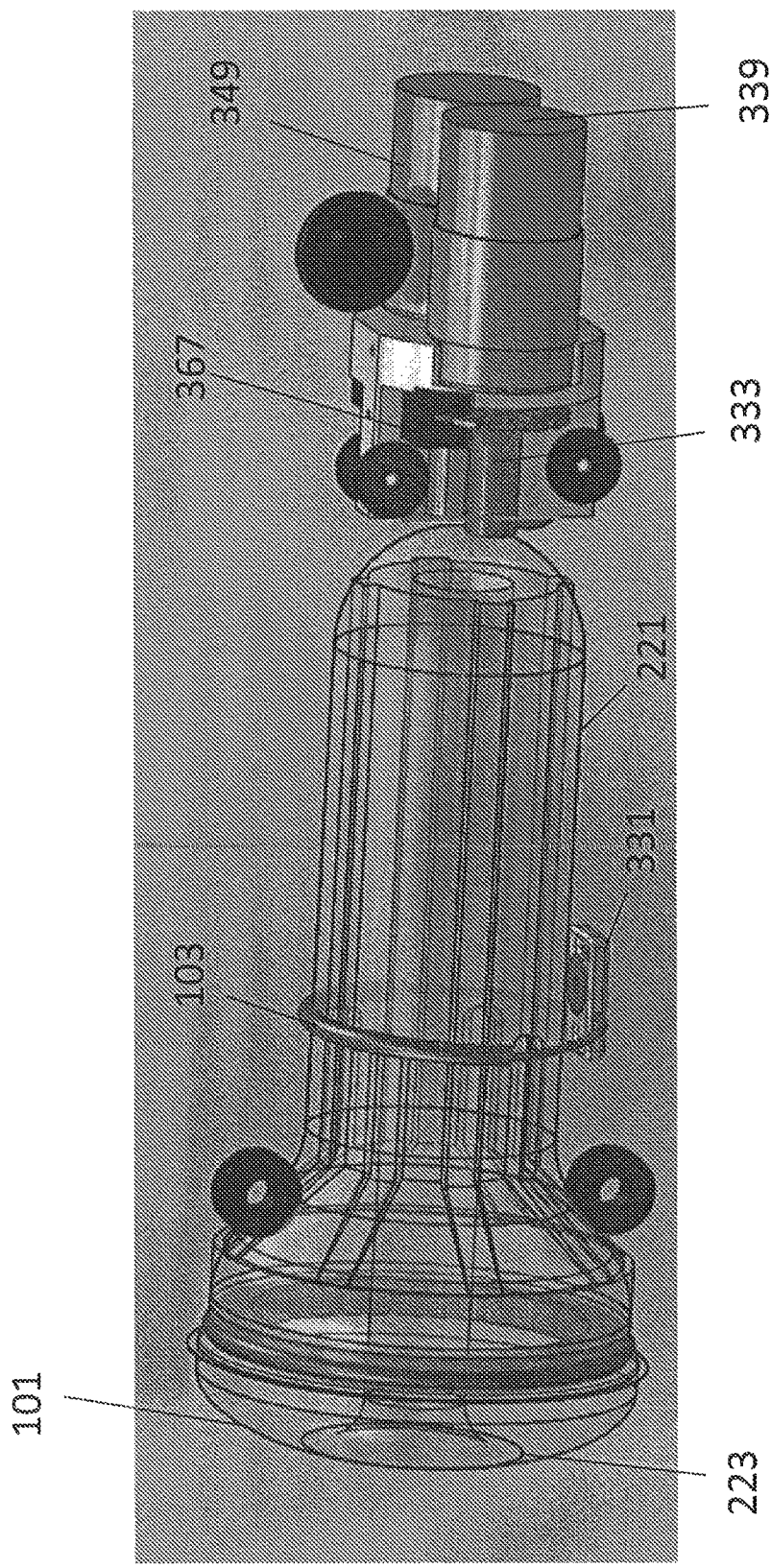
FIG. 2 shows the device of FIGS. 1A and 1B with the outer housing removed.
Figure 3:
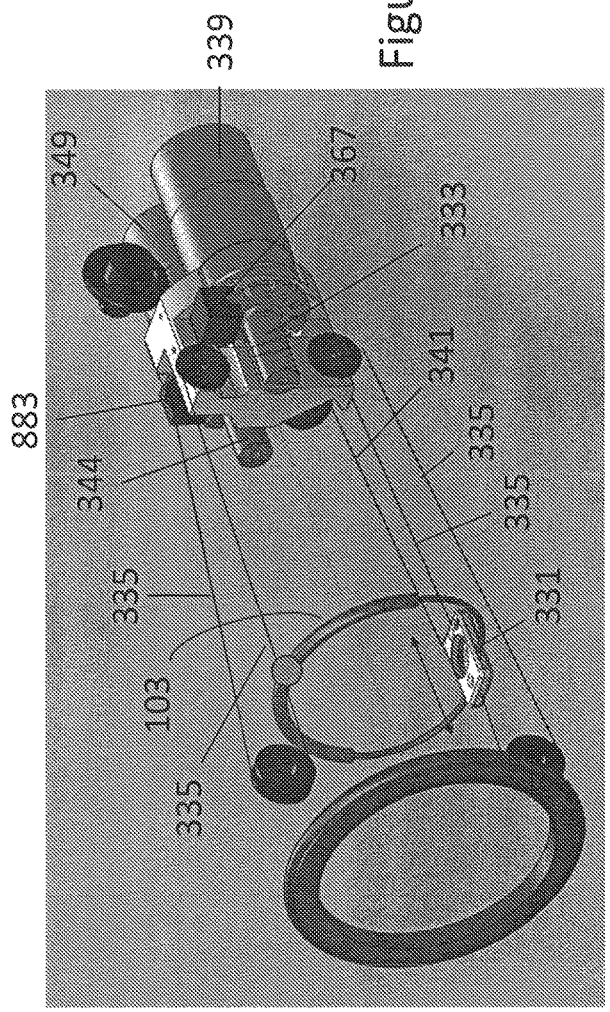
FIGS. 3A and 3B show the pulley system of the device of FIGS. 1A and 1B.
Figure 4:
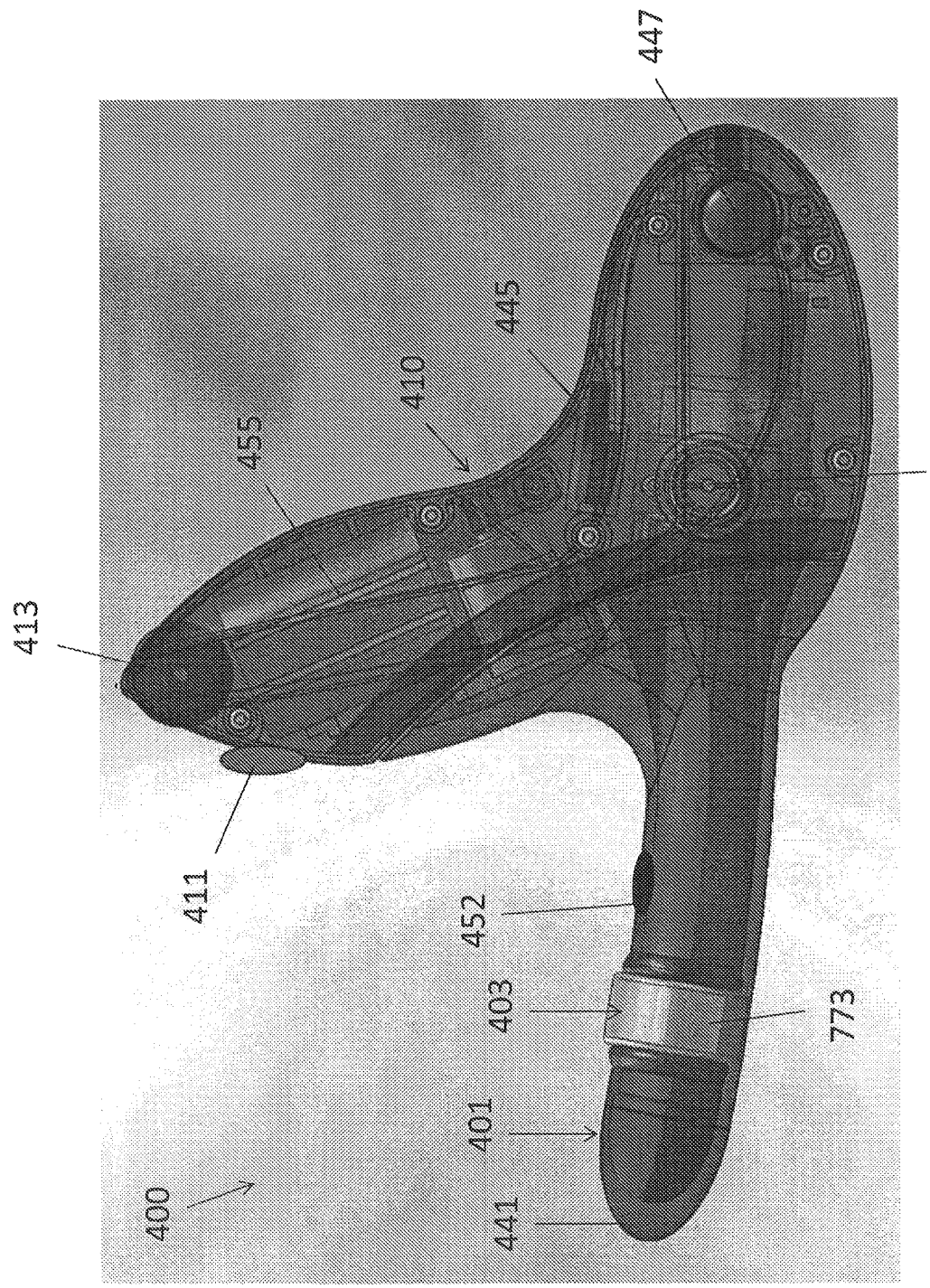
FIG. 4 is a transparent view of another embodiment of a device for sexual stimulation.
Figure 5:
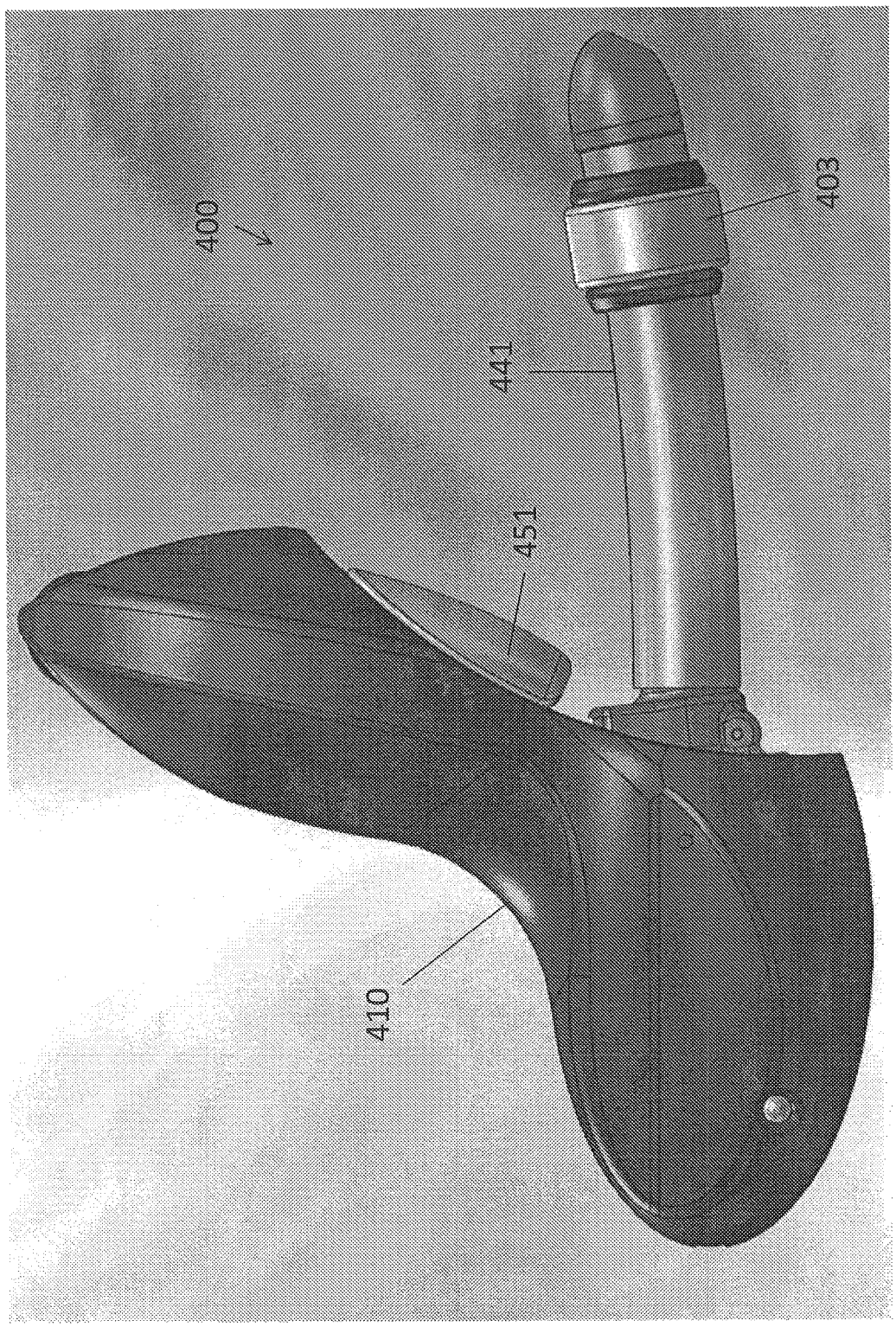
FIG. 5 is an exterior view of the device of FIG. 4.
Figure 6A:
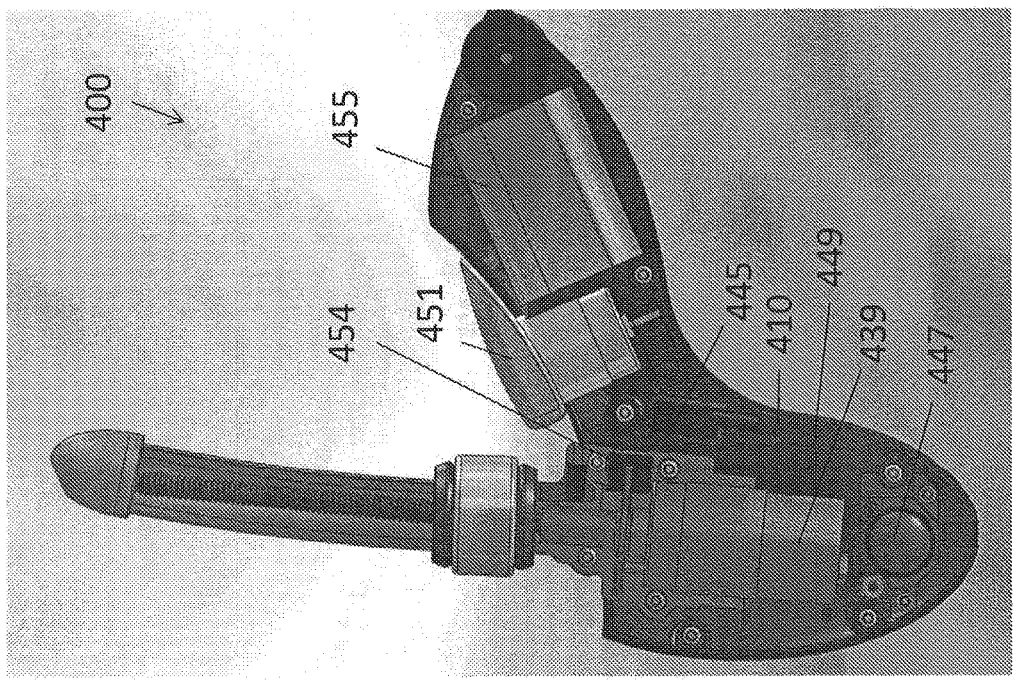
FIGS. 6A and 6B show the device of FIG. 4 with a portion of the handle and the outer sheath removed. The ring is of the device is shown in FIG. 6A in a distal position while the ring is shown in FIG. 6B in a proximal position.
Figure 6B:
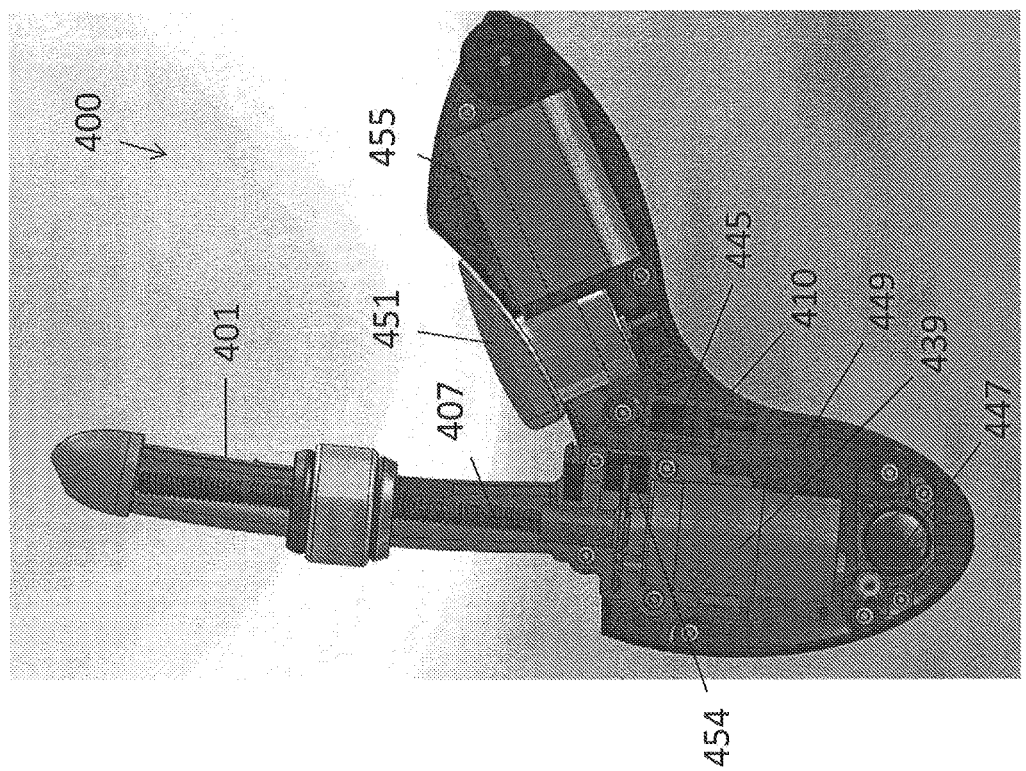
Figure 7:
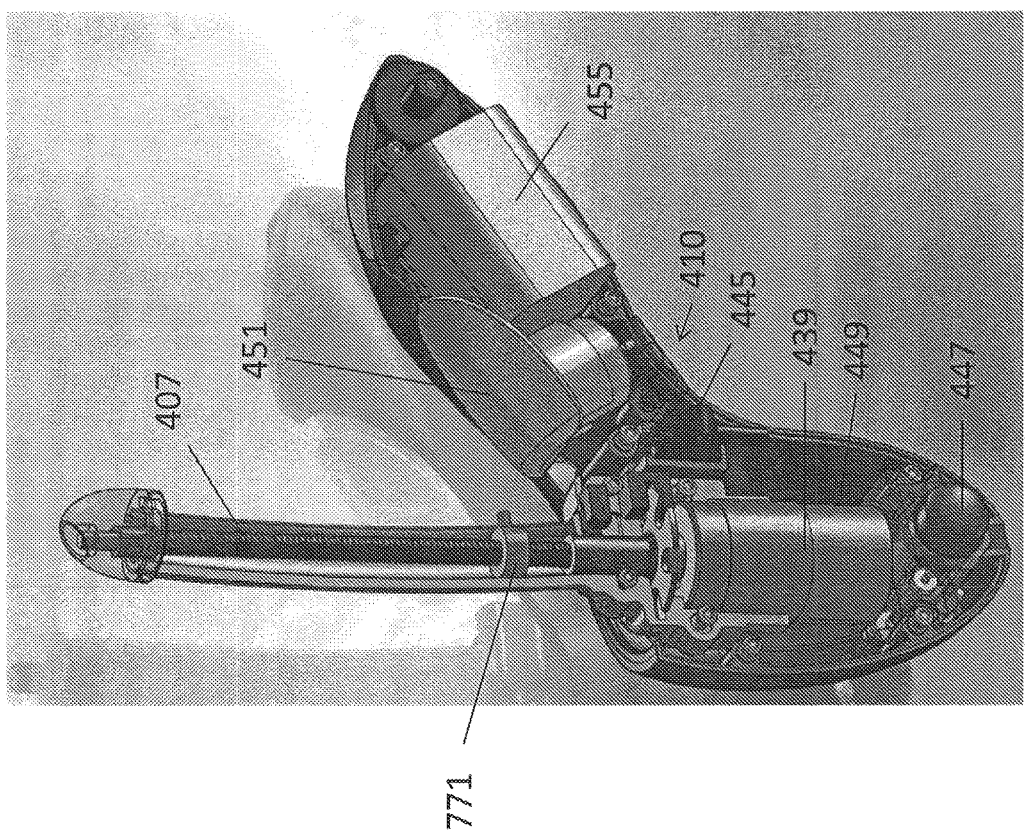
FIG. 7 shows the device of FIG. 4 with the outer ring, sheath, and portions of the handle removed to show the inner screw and nut of the elongate shaft.

In general, described herein are sexual stimulation apparatuses (including devices and systems). These devices (which can also be referred to as sex toys) generally include a ring having a diameter (inner diameter, outer diameter, or both) that can be modified, as well as a longitudinal axis along which the ring may move axially. In general, these devices also include an axial actuator for moving the ring in the longitudinal axis, as well as a ring diameter actuator for changing the diameter of the ring. The device may also include or more controls for controlling the longitudinal position and diameter of the ring. The control may be automatic or manual, or may be responsive to communication between devices or from a server or other outside source.

The ring may be referred to as a stimulation ring, expandable ring, contracting ring, or the like. The ring may be a toroid, an O-ring, a doughnut shape, or the like. In general, the ring shape is formed having a central opening and a roughly round cross-section (or oval cross-section), however, the ring does not have to be continuous. For example, the ring may be formed of a wire or other member whose ends are separated (and may be coupled to a ring diameter actuator; the ring diameter actuator may expand/contract the ring by increasing or decreasing the length of the material forming the ring. In some variations, the ring is expandable/contractible by a ring diameter actuator that inflates/deflates (e.g., pneumatically, hydraulically, etc.) the ring. In general, the ring may be covered or surrounded by one or more elements or covers, including a membrane or the like. A cover may generally be configured to expand/contract with the ring. In general, either the ring, the ring diameter actuator, or both may also include one or more sensors for detecting the diameter, or a change in the diameter of the ring. In some variations, a ring diameter sensor may be used in a feedback look for controlling the diameter of the ring.

The longitudinal axis of the apparatus may generally be formed by an elongate member than can be structured as either an inner member (e.g., rod, axel, central member, tube, arm, beam, boom, column, elongate body, etc.) or an outer member (e.g., tube, pipe, hose, duct, channel, frame, etc.). The elongate member(s) forming the longitudinal axis may act as a track along which the ring can move axially, and may therefore be referred to as a track member forming the longitudinal axis. The track member may be configured so that it couples to the ring. The ring can move while remaining perpendicular to the track member as it moves in the proximal to distal direction along the track member. The track member may generally be straight, bent, curved, or the like, while extending in an axial to distal direction. The track member is generally rigid, though in some variations it may be flexible. The track member may form part of the actuator, and may include gears, gearing, cables, or other engagement regions or members to which an axial actuator can engage to drive the ring member proximally and/or distally.

For example, in some variations the track member (e.g., an elongate member and/or sleeve member) may be configured so that the stimulation ring controllable slides proximally and distally as driven by the axial actuator. The axial actuator may include one or more mechanical drivers (e.g., gears, pulleys, etc.), electrical/magnetic drivers (magnets, inductors, etc.), and/or pneumatic/hydraulic drivers, or the like. In general, these devices may be configured so that the movements (axial and/or ring diameter) are controlled by a controller.

A controller may be an electrical controller, which may include hardware and/or software and/or firmware for controlling the movement and/or position and/or shape (diameter) of the ring relative to the proximal/distal axis of the apparatus. In some variations, the controller may coordinate both the axial position/movement and the radial dimension(s) of the ring. Alternatively, in some variations, separate controls (or control sub-systems) may be used.

Any of the variations of the apparatuses described herein may also include one or more manual controls located on the apparatus. For example, manual controls may include controls driving (separately or in combination) the ring diameter, the axial position of the ring, etc. In some variations, the controls may also be configured to trigger an automatic movement function, driving the ring (position/axial movement/diameter) automatically in a predetermined (and/or random) pattern.

In general, any of the devices and apparatuses described herein may also be configured to communicate with each other and/or with other systems. Thus, the device may be configured to control the movements and/or positions of the ring or other elements based on outside input and/or may transmit the movements and/or positions of the entire device and/or regions of the device (including the movement and/or position of the ring). In some variations, the device are configured for duplex (e.g., full duplex or half duplex) communication.

Any of the apparatuses described herein may communicate by any appropriate technique, including radio (e.g. RF, Bluetooth, etc.), optical, sonic (e.g., audible), or the like. The devices may include one or more processors configured to encode/decode signals and also one or more receivers/transmitters (or transceivers) configured to operate in the appropriate communication modality. For example, an apparatus as described herein may include a communication processor configured to encode and/or decode signals describing the movement of the overall device, axial position of the ring, axial movement of the ring, diameter (outer and/or inner) of the ring element, etc. Examples of the methods of communication by and between apparatuses and/or outside units are described below.

In general, the apparatuses described herein may be configured as "female" devices or as "male devices". As will be described in greater detail below, the female device may be configured to have a channel or opening; thus the elongate member forming the longitudinal axis is configured with a central channel or passage that includes the ring therein. In contrast, the "male devices" may be configured as an inner tubular or solid member over which the opening in the ring slides.

Female Device

A female device as described herein is designed to mimic a portion of the female anatomy and can be used for sexual stimulation of a user. The device includes a flesh-like tube with one or more actuated, closed loop, local processor controlled massage actuators positioned outside of the tube. Further, the device can include two degrees of freedom: a translation axis and a constrictor axis.

Referring to FIGS. 1A-3B, a female device 100 includes an elongate body 101 and a ring 103 configured to translate along the elongate body 101 and constrict over the elongate body 101. The elongate body 101 can include an open-ended tubular member 221 (i.e., having an opening or channel therein) and an inner sleeve 223 within the opening or channel. The sleeve 223 can be attachable and detachable from the tubular member 221. The tubular member 221 can be made of Teflon and can have a sock-like shape with a flange at the proximal end (the sleeve 223 can be attached to the flange). The tubular member 221 can further be pleated or otherwise compressible so as to allow constriction thereof. The sleeve 223 can be made of a soft, pliable materials, such as mineral gel oil. For example, the sleeve 223 can be made of a flesh-like material having a durometer of between 5 and 40 shoreA or 10-50 ShoreOO. The opening or channel within the elongate body 101 can be configured to mimic a portion of female anatomy, such as a vaginal canal.

The ring 103 can be made of a plastic material, such as polytetrafluoroethylene, and can include a shuttle 331 attached thereto. The shuttle 331 can be connected to a shuttle cable 335. Further, a pulley arrangement in the device 100 can allow a translation actuator or motor 339 to wind the shuttle cable 335 on a capstan 333, thereby providing translation of the shuttle 331 and the ring 103. A tensioning spring can provide the required tension on the shuttle cable 335 to allow the capstan 333 to transfer power to the shuttle cable 335.

In some embodiments, the device 100 can include a rotation encoder 367, such as an incremental two channel optical encoder, to sense the position of the motor 339, and thus sense the position of the ring 103. The device 100 can further include a controller 881 (see FIG. 17), such as a small printed circuit board, configured to run a control loop to keep the shuttle 331 position located at the target commanded location along the longitudinal axis 105 of the device 100. Using information from the sensors 267, the controller 881 can control the location of the shuttle 331, thereby controlling the axial location of the ring 103. The controller 881 can be capable of slewing the ring 103 from one position to another at speeds at least as high as would be measured for actual copulation. For example, the controller 881 can slew the ring 103 from proximal end to distal end and back in <0.5 seconds and can have a frequency response of >5 Hz. The device 100 can, for example, reproduce and transduce sensed forces from 0 Hz to greater than 10 Hz with a frequency response from DC to 100 Hz.

The ring 103 can include a constriction cable 341 running therethrough. Further, the shuttle 331 can include a pulley 343, which can be connected to the constriction cable 341. A separate control system including a constriction actuator or motor 349 can be configured to real the constriction cable 341 in and out at the same rate as the shuttle cable 335, thereby keeping tension in the ring substantially constant. An encoder 883, such as an optical encoder, can detect the relative position of the constriction cable 341, and thus of the amount of constriction of the ring 103. The controller 881 can modulate tension in ring 103 to constrict and relax the ring 103 from a diameter of approximately 15 mm fully closed to an open diameter of approximately 60 mm.

In one embodiment, the ring 103 can be comprised of two telescoping tubes, such as 1/16" OD Teflon tubes of 30 mm length, inserted into the shuttle 331 at one end and into a larger 1/8"OD Teflon tube at their other ends. The constriction cable 341 can be terminated at one end on the shuttle 331 by a crimp, pass through the telescoping tubes, re-enter the shuttle 331, loop around the pulley 343, and exit the shuttle for connection to a capstan 344 connected to the motor 349. As the constriction cable 341 is tensioned, the tube assembly of the ring 103 also constricts.

In some embodiments, a fixed length outer cable sheath can be placed between the shuttle 331 and the pulley system. The fixed length sheath can be helically wound around the elongate body 101, winding and unwinding as the shuttle 331 is translated. This fixed length outer cable sheath can advantageously reduce the need for the controller to keep track of slack or initialize the position of the ring 103.

The controller 881 can be configured to constrict and relax the ring 103 rapidly similar to real muscular response of a pubococcygeus muscle in a vaginal canal. Further, because the two controlled axes are independent, the ring 103 is able to travel along the elongate body 101 while also expanding and contracting as desired. The tubular member 221 provides a very low friction barrier between the insert 223 and the moving ring 103. With this arrangement, the user experiences realistic constriction along an anatomically realistic length.

In some embodiments, the device 100 can include a home sensor 151, such as a Hall Effect sensor, configured to be responsive to a magnet attached to the shuttle. The controller 881 can be configured servos the shuttle on startup until the home sensor generates an interrupt signal, which resets the encoders 367, 883.

In some embodiments, a position sensor 885 can be used to determine the penetration position or penetration of a user, e.g., the user's penis, into the device 100. The sensor 885 can be, for example, an accelerometer that, in combination with double integration, provides a penetration or position control variable output signal to be sent to a paired device. That is, the accelerometer, when doubled integrated, can detect a relative change in distance of the accelerometer, and thus a change in distance of the user relative to the device 100, over time. This change in distance over time can be used to detect the relative penetration of the user, e.g., of the user's penis. This penetration distance can then be output to a paired device, as described further below. In some embodiments, the position sensor 885 can be mounted on a printed circuit board, such as on the controller 881.

The motors 339, 349, sensor 885, encoders 367, 883, and various pulleys and cables can advantageously be located outside sleeve 223 by virtue of the cable routing/mechanism design described herein. The tubular member 221 advantageously provides needed friction control as well as a moisture barrier. This design can be complimentary and compatible with the existing high volume shipping female-like products. The form factor for the device can be additive in applications to realize a full robotic system capable of simulating intercourse.

As described further below, the ring 103 can be responsive to a remote signal via the internet or an audio carried frequency modulated telemetry system. The ring 103 can change diameter based on the level and rate of change of pressure measured in a paired device. Firmware scaling, use of differentiator op-amp circuit, and other firmware means can modify the magnitude and rate of constriction. In one embodiment, the ring 103 mimics the tightness of the vaginal canal of the woman using the paired device. Further, the sensors can be used to convey information regarding the constriction or placement of the ring 103 to a paired device.

In some embodiments, the device 100 can be run both in a "paired mode," i.e., actuate in response to a paired device and a "manual mode," i.e. actuate without signals from a paired device. Manual mode can be activated, for example, by automatic detection by the controller 881 that no carrier frequency is detected.

In some embodiments, the ring can include helical springs on one or both sides to help with relaxation and opening of the ring. In some embodiments, the device 100 can include a force sensitive resistor (FSR) pressure sensor for manual mode control of constriction.

The device 100 advantageously provides a compact, quiet, high force, very high bandwidth, bio-mimetic actuation system capable of simulating and literally transducing biometric signals from the similarly enabled paired male device providing control signals.

The female device 100, in some embodiments, can be designed to make intimate contact with male anatomy, such as by accepting insertion of penis or by retaining itself to anatomy in order to press against the penis, the base of the penis, or other sexually stimulating anatomical regions.

Male Device

A male device as described herein is designed to mimic a portion of the male anatomy and can be used for sexual stimulation of a user. The device includes an elongate body and a translatable ring configured to expand relative to the elongate body.

Referring to FIGS. 4-7, a male device 400 includes a curved prismatic body 401 rotatable coupled to a handle 410. An expandable, e.g., inflatable ring 403 is translatable along the body 401.

The prismatic body 401 can include a relative soft distal tip 471 configured to mimic the tip of a male penis. The shaft of the prismatic body 401 can include a lead screw 107 therein, which can be connected to a motor 439. The ring 403 can include a translating drive nut 771 (see FIG. 7), such as attached to the balloon 773. The nut 771 can include an anti-rotation pin. The drive nut 771 can be located around, and translatable along, the lead screw 107. Thus, as the lead screw 107 is rotated by the motor 439, the nut 771, and thus the ring 403, can translate along the elongate body 401.

The ring 403 can further include an expanding diameter balloon 773. Thus, the balloon 773 can have a fluid or air conducting tube 449 connected to an inflation mechanism 447 and a sensor 445 to detect the pressure of the balloon. In one embodiment, the pressure sensor 445 can be connected to an op-amp differentiator circuit stage that amplifies and differentiates the raw pressure sensor signal from the balloon. This can advantageously boost the change in pressure and remove the offset or constant portion of the pressure signal. The differentiator circuit can include both high and low pass characteristics, allowing for a large output signal for subtle changes in pressure around any given mean pressure and rolling off higher frequencies, such as frequencies about 100 Hz. Further, in one embodiment, a pressure differentiator circuit associated with the sensor 445 can produce a large amplified signal that represents change in balloon pressure. The circuit can be configured such that a basic pressure signal is added to the differentiated signal to form a PD output. Advantageously, this allows some output from the sensor for slowing changing pressure and significant output for rapid changes.

The ring 403 can be either passively larger than the prismatic body or actively expanded and contracted to desired or controlled girth, volume, shape, or hardness. In some embodiments, the ring 403 can have an unexpanded or uninflated volume of approximately 30 mm and an expanded or inflated volume of approximately 60 mm.

The handle 410 can be connected to the prismatic body 401, which can be rotated or angled relative to the handle 410 about a rotation axis 444. The handle 410 can be configured to provide ease of holding and control from many angles and positions. The handle 410 can further included a dented portion configured to sit in between a user's legs. The handle 410 can include a manual control 411, such as a finger pad or button, configured to manually control the position of the ring 403. A control potentiometer 413 can be connected to the control 411 to change the location of the ring 403. In addition to use in manual mode, the translation of the ring 403 can be controlled automatically in response to features of a paired device, as further described below. The handle 410 can further include a vibrating element 451 suspended at least in part in the sheath 441. The vibrating element 451 can be, for example, an eccentric rotating mass vibration motor or can be a motor grounded to the handle 410 through a living hinge. In some embodiments, a female user can position the vibrating element by onto the clitoris by adjusting the rotatable shaft position. The handle 410 can further include the inflation mechanism 447, which can inflate with a piston and deflate with a pressure relief valve to control inflation of the balloon 773. The inflation can be controlled, for example, through a pneumatic module having a piston, two check valves, and a release button. In one embodiment, the user can push the piston about 10 times to inflate the balloon to about 60 mm diameter and press a release button to deflate it.

The prismatic body 401, lead screw, 407, and ring 403 can be enclosed within a flesh—like stretchable sheath 441 made, for example, of a material having a durometer of between 5 and 40 shoreA or 10-50 ShoreOO, e.g., a material made of mineral gel oil. In some embodiments, the sheath 441 can enclose a friction reducing lubricant.

A controller 991 (see FIG. 17) can be configured to be responsive to pressure or constriction of the balloon housed under the sheath and/or prepare telemetry signals to send over telephonic or internet connection to a paired device designed to respond to the signals. Further, an encoder 454 can be used to detect the position of the ring 403 (via a measurement of the rotation angle of the lead screw). The detected position 454 can be used as an input for closed-loop control by the controller 991.

Thus, the lead screw 407, nut 741, motor 439, encoder 454, and controller 991 provide closed loop position control of the translation and expansion of the ring 403. Either local control via the pressure sensitive control interface or remote control can set the target position of the translating ring. The device 400 is advantageously capable of high bandwidth transduction of realistic intercourse simulating insertion with slew rate from proximal to distal end in <0.5 seconds with a bandwidth of >5 Hz. The device 400 can, for example, reproduce and transduce sensed forces from 0 Hz to greater than 10 Hz with a frequency response from DC to 100 Hz In some embodiments, the device 500 can include an electromechanical inflation means that would be responsive to a remote control signal. In some embodiments, the user can expand or inflate the ring to desired girth and then experience either local control of translation or remote control of translation (such as in response to signals from a paired device). The device 400 can thus be a stand-alone device or remotely controlled.

The device 400 can further include a pressure sensor 445 to measure the pressure or inflation of the ring 403. The pressure sensor 445, in combination with an amplification circuit and differentiation circuit response to the change in pressure, can provide a signal proportional to the rate of change of pressure. Because tighter vaginal canals would naturally produce higher pressure offsets in the signal, differentiation can eliminate DC offsets and effectively generate a AC coupled signal that is a change in pressure signal. The pressure signal generated can be sent to a paired device, such as to a paired female device, to control the features of the paired device. In one embodiment, the ring 403 mimics the hardening or expansion of the penis of a man using the paired device.

In some embodiments, the device can further include a sensor 452 configured to detect the penetration of the device into a user, such as into a female user's vagina. The sensor 452 can be, for example, an accelerometer that, in combination with double integration, provides a penetration or position control variable output signal to be sent to a paired device. That is, the accelerometer, when doubled integrated, can detect a relative change in distance of the accelerometer, and a change in distance of the user relative to the device 400, over time. This change in distance over time can be used to detect the relative penetration of the device into the user, e.g., into the user's vagina. This penetration distance can then be output to a paired device, as described further below. In some embodiments, the position sensor 452 can be mounted on a printed circuit board, such as on the controller 8811.

In some embodiments, the ring 403 can be replaced with a chamber part in the sleeve that is pulled and pushed by a collar. In some embodiments, the lead screw can be replaced by a cable drive. In some embodiments, the handle portion can be extended to house larger batteries and provide a comfortable grip. In some embodiments, an accelerometer can be included in the handle for stroke variable.

The device 400 is advantageously provides a compact, quiet, high force, very high bandwidth, bio-mimetic actuation system capable of simulating and literally transducing biometric signals from the similarly enabled paired female device providing control signals.

The male device 400, in some embodiments, can be designed to make intimate contact with female anatomy, including by inserting into the vagina or by pressing against sexually involved areas around the outside of the vagina like labia or clitoris. The shape of the male device 400 can also be convenient for making contact with the anal region.

Power Supply and User Interface for Devices

Each device 100, 400 can be separately powered by power cord, battery (such as battery 455 shown in the device 400), capacitor, solar, or other means, with the intention that power cables to the device are minimized. If the device contains a means of energy storage that requires charging, charging is preferably done inductively or through other means that does not require exposed electrical contacts, so that the devices are sealed. Exposed electrical contacts are acceptable if properly sealed. Charging without a base station may be preferred for discreteness.

Each of the devices 100, 400 can have a simple user interface that includes a power switch, a battery level indicator, an indicator for status of connection to local host computer, a button to pair with local host computer, a mode selection button(s), a button(s) to adjust magnitude of user experience—how much of AC and DC dynamic range of actuators is used, a button(s) to adjust tempo of user experience—nudge the nominal tempo (established by network transmissions) up or down, and/or an orgasm button.

Sensor Technology

Various sensors can be included on the devices 100, 400 in addition to, or in place of, the sensors described above. These sensors can sense or monitor both physical signals and sexual effectiveness signals.

Physical signals from the devices 100, 400 can include measurements of position, velocity, acceleration, frequency, orientation, length, circumference, stiffness, pressure, force, etc. These physical qualities may be represented in absolute or relative scales. In the preferred embodiment, a device may have a plurality of sensors arranged in a way that enables combined sensor signals to be measured, similar to how quadrature encoders combine signals from multiple phased emitter/detector pairs.

The devices 100, 400 (or other similar devices) can further include additional sensors to measure sexual effectiveness. Historically, ECG or EEG, respiration rate, breathing exertion (see sleep studies), blood oxygen saturation, have all been used to sense degree of sexual arousal and climax. Blood flow sensors such as "photoplethysmograph" or muscle activity sensors "electromyography", have been used in the past. Moisture sensors could be used as well.

The physical sensors can be used for monitoring stroke rate and force over time, in order to identify sexual climax. It is expected that these parameters would progressively increase over time until a peak is detected, then quickly fall off once climax was achieved. There may be lag between orgasm and when the sensors identify the downslope. There may be false positives if a user gets tired and stops, or is interrupted.

Heart rate may also be used as an assessment of degree of stimulation of a user. Heart rate increases with sexual stimulation and decreases after orgasm. If our novel sensors are designed to offer high sensitivity in the 40-240 Hz bandwidth, they may be used to sense heartbeat.

Temperature sensors can be used to measure temperature, which increases with increased blood flow to the penis or vaginal areas as accompanied with sexual arousal. By configuring our novel strain sensor not to strain due to physical perturbation, any sensed strain must come from thermal strain.

In some embodiments, users can give input to identify orgasm to more finely tune the devices. One inexpensive and reliable way to do this is to allow the user to give feedback via UI on the sex toy, for instance, the "orgasm button". User may press the orgasm button—even bang on it to communicate stronger effect—if she wants to "star" a session for later playback, or communicate to her partner of the success they achieved together. The controls or servers used with the devices may also benefit from knowing this feedback, e.g. which sorts of inputs are helpful for pre-orgasmic women to progress through a therapeutic plan.

One type of physical sensor that can be used is a semiconductive elastomeric sensor to detect a change in strain of a portion of the device (such as the inner sleeve 223 of the device 100 or the sheath 441 of the device 400). The elastomeric sensors described herein can be soft, flexible, and stretchable.

Referring to FIGS. 8a-8c, a sensor 800 can include a laminate of a substrate 801 supporting or encasing a semiconductive tape layer 803 to form at least a partially sealed and supported sub-assembly. The substrate 801 can be, for example, a self-fusing silicone tape, fluorosilicone, or polyurethane. Further, the semi-conductive tape layer 803 can be, for example, made of a material that is inherently resistant to degradation from contact with oil gel materials. The semi-conductive layer 803 can include a semi-conductive rubber material, such 3M's Scotch 13 tape. The substrate 801 can apply the pressure required to electrically bind fine wire connections of the sensor 800 to the semi-conductive tape. By placing contacts on the semi-conductive layer 803 and then stretching it, the layer 803 advantageously behaves like an unusually compliant force sensitive resistor (FSR). Off the shelf, the substrate material, such as 3M's tape material, can be viscoelastic and thus mechanically weak and unstable over time. When sandwiched within a substrate 801, e.g. self-fusing silicone tape, latex rubber, or molded silicone, the semi-conductive tape layer 803 can advantageously be stabilized to realize repeatable operation as a sensor 800, tolerating repeated cycles and returning to its original shape after deformation.

Advantageously, addition of electrodes 805 in the lamination merely requires pressure, not solder or laser weld or other, to make reliable electrical contact between the semi-conductive tape 801 and electrical connections. Advantageously, the resulting sensor 800 can be soft, pliable, formable or moldable into various shapes and structures, and electrically connected in an unobtrusive way. Advantageously, through the use of thin materials, such as materials made by dip molding, the sensors described herein can be used for a sexual devices, such as devices 100 or 400 or a condom, to incorporate an array of sensors that respond to the various nuances of sexual intercourse.

Springs in parallel work additively. If the anatomy is modeled to have a spring stiffness Ka and the sensor/substrate is modeled to have a spring stiffness Ks, we want Ks to be a) equivalent to, or b) substantially less than, Ka. This requirement is important to ensure that the sensor/substrate a) feel like naturally mating anatomy, or b) are substantially unnoticeable and unimposing, respectively. The sensors described herein can advantageously meet both of these requirements.

In one embodiment, the sensors described herein, such as sensor 800, can be manufactured by wrapping a layer of self-fusing silicone tape around a mandrel. Then, the semi-conductive tape can be laminated to the silicone tape. Lastly, another layer of silicone tape can be laminated on top of the semi-conductive tape. The mandrel, can be first covered with a layer of Teflon tape to help the sticky silicone layer to slide off the mandrel.

FIG. 8*a* shows the simplest embodiment of a sensor 800 where two electrodes 805*a,b* are placed along the semi-conductive layer 803. The resistance can be measured between them, such as by using a voltage divider. The electrodes 803*a,b* may be widened to pick up average strain over a larger section of material if desired.

Referring to FIG. 8*b*, in some embodiments, multiple sensors can be formed by placing more than two electrodes 805*a,b,c,d* on the same laminate. By having more electrodes in the same area, such as an array of sensors, higher resolution per area can be obtained. As shown in FIG. 8*b*, the electrodes 805 can be arranged linearly to track a single strain direction. In contrast, as shown in FIG. 8*c*, electrodes 805 can be arranged on the laminate in a more complex array to track different directions of strain and shape deformation. In this scenario, the multiple electrodes can be multiplexed.

As shown in FIGS. 9*a*-9*e*, one basic deployment strategy is to form ring sensors 900 with the laminate 901/903 and electrodes 905. In one embodiment (shown in FIG. 9*a*), these rings can be placed along a phallic shaped device that could be inserted into anatomy, say vaginally or anally. In another embodiment (shown in FIG. 9*b*), these rings could be placed on a device designed to accept the introduction of anatomy, such as a penis. For example, when the penis is inserted and the rings expand, strain can be sensed in the form of a resistance change described above.

Further, as shown in FIG. 9*c*, multiple ring shaped sensors can be grouped together into an array that can sense, for example, the amount of insertion of a penis over time or the degree of insertion of a phallic device into the vagina. By looking at the correlation in "strain from baseline" between sensor pairs, the tip of the penis can be localized. Once this degree of insertion is known, it is also straightforward to determine velocity of insertion by computing change in degree of insertion over time. Stroke length can also be computed by observing the extent of position between direction changes. Measuring the time between direction changes can yield stroke frequency.

Referring to FIG. 9*d*, in some embodiments, a history of motion can be computer and recorded by an onboard microprocessor dedicated to reading this information from a single sensor or group of sensors 905. The onboard microprocessor will also be used to access stored calibration and configuration data for each sensor, in order to make its measurements. It can also do requisite multiplexing.

Ring-shaped sensors can advantageously detect both localized force (as shown by the force arrow 911 in FIG. 9*d*) and radial force (as shown by the force arrows 913 in FIG. 9*b*).

Thus, in one embodiment, localization can be obtained by looking at relative difference in signal between an adjacent pair of sensors according to equation 1:

$$\frac{\varepsilon_n - \varepsilon_{n+1}}{d_{n,n+1}} \quad \text{(equation 1)}$$

In some embodiments, it can be useful to track strain over time for a single "C" or ring-shaped shaped sensor, such as in order to measure the growth of penis girth or constriction of a vagina. With semi-conductive tape laminated to an elastic (non-plastic) substrate of well-characterized stiffness, accurate readings on girth of penis or vagina can advantageously be made.

In some embodiments, stiffness can also be measured. Stiffness is the displacement measured in response to force applied. If an actuator is collocated with one of these ring sensors 900, the actuator can be commanded to produce a known force. The ring sensor 900 output can in turn be measured to find the tissue displacement. It may be important to subtract the displacement-per-force when no tissue is present, in order not to measure the substrate stiffness.

As noted above, localized force or pressure can be measured in addition to position and shape sensors. For example, such calculations can be useful in determining how much force is being applied by the base of a man's penis at the entrance to a simulated vagina. The semi-conductive material is naturally a force sensor, but it works better in stretching than compression. Two approaches may be pursued: laminating the semi-conductive material to a cantilevered substrate of known stiffness, or placing the semi-conductive material on an inflexible substrate so that force compresses the material. Either of these lamination stacks can be placed in regions where force information is desired, like at the base of the penis.

FIG. 9*e* shows how arrays of these sensors can be extended to very high resolution and broad areas. In this manner, a fully instrumented condom could be constructed. Flexible, electrically conductive ink could be the key to realizing this design.

The ring sensor 900 can have optimum sensitivity, dynamic range, signal-to-noise ratio (SNR), and bandwidth. In one exemplary embodiment, the sensor 900 is formed into a band of approximately 40 mm diameter and 10 mm width. Only grams of force can be required to begin to see change in resistance. The resulting signal can swing dramatically from 5 Mohm to 1 Mohm with only ~10% diameter strain. Deformations such as twisting and collapsing the band advantageously have very little effect on the output signal, while stretching produces a large signal. This behavior, that the sensor produces large output from desired strains while rejecting motions that could potentially produce unwanted signal (noise), is highly desirable and makes for an excellent signal-to-noise ratio (SNR). Bandwidth is inherently very high for an analog sensor like this, but the ultimate practical limit to how quickly successive measurements are made is how quickly the whole sandwich (supporting material+semi-conductive sensor) can rebound. The rebound can be controlled carefully through use of the substrate 901.

Parameterized sensor output can be applied, for example, by storing it for replay, analyzing it to ascertain populations of anatomical features or sexual behaviors/experiences, sending it over the wire for replication by a slave actuator set, or communicating it real-time for full duplex teleoperation.

To transmit data, each sensor value can be individually sent to a slave or tele-operated device. Alternately, to reduce payload, sensor values maybe parameterized into an equation through a fitting process, perhaps done within the microprocessor. Position as degree of insertion (P), stroke length (£), stroke frequency (f), phase or mapping (ϕ), can form parameters of oscillatory equation 2:

$$P = l\sin(2\pi ft + \phi). \quad \text{(equation 2)}$$

Then, in one embodiment, no matter how many sensors are in a device, only these few parameters need be sent. A paired device, perhaps with different sensor or actuator count, can deploy the received parameters to replicate the experience given its own unique configuration.

In some embodiments, the sensors 800/900 described herein can be wrapped helically around a hollow cylindrical body and can be attached either at the ends or continuously along the elongate body. The sensor can thus be responsive to strain by local and accumulated expansion of cylinder. The helical arrangement can be advantageous, for example, because as a penis is inserted into canal, incremental portions of the semi-conductive sensor will stretch and accumulate a total strain, causing a total measurable resistance change that is proportional to insertion depth.

In some embodiments, the sensors 800, 900 can be a silk screened assembly of highly electrically conductive row and column electrodes, insulated from each other where they cross over, where each row is joined to a column by N semi conductive silk screen printed regions. The processor can poll each row and column and read the resistance of each element to build an image of strain and pressure.

The sensors described herein are safe and low-cost sensor are extremely well suited to measure biometric/physiological interactions between a human and a human-operated device. When incorporated into a device such as a sex toy, or even a diagnostic or therapeutic medical instrument, organized interrogation of these sensors can measure position, as degree of insertion: into the vagina, over the penis, or with respect to other anatomy that comes in contact with the device, location of a point contact with the device, force/pressure of a point contact with the device, stroke length, stroke velocity, stroke frequency, anatomical length, as length of penis, vaginal canal, anus, etc., anatomical girth, as diameter of penis, vaginal canal, anus, etc., change in anatomical length or girth, such as when aroused for sex or engaging in sex, and/or localized issue stiffness, when paired with a calibrated actuator that is capable of displacing both the tissue around the device and the devices sensor, simultaneously.

The sensors or group(s) of sensors, can be interrogated by a neighboring microprocessor. The microprocessor can be responsible for reading input from individual sensor elements, applying calibration factors and scaling, interpreting each sensor element input with respect to its location on the device, and combining its processed output with the same output from multiple other sensors. In this way, the metrics described above can be measured in suitable absolute or relative sense. Further, the microprocessor may then communicate the metrics over a network for use in the particular application.

The sensors described herein can also include or be paired with other known biometric sensors to measure a broad set of physiological changes that accompany sexual arousal: heart rate, body temperature, blood flow, muscle activity, respiration rate, breathing exertion, moisture, ECG, EEG, blood oxygen saturation, etc. This sum-total sensor data set, or any portion of it, can be used, for example, in a localized control loop within a single device, in a tele-robotic scenario between or among multiple devices, or accumulated across multiple users and use sessions.

Communication

Figure 17:
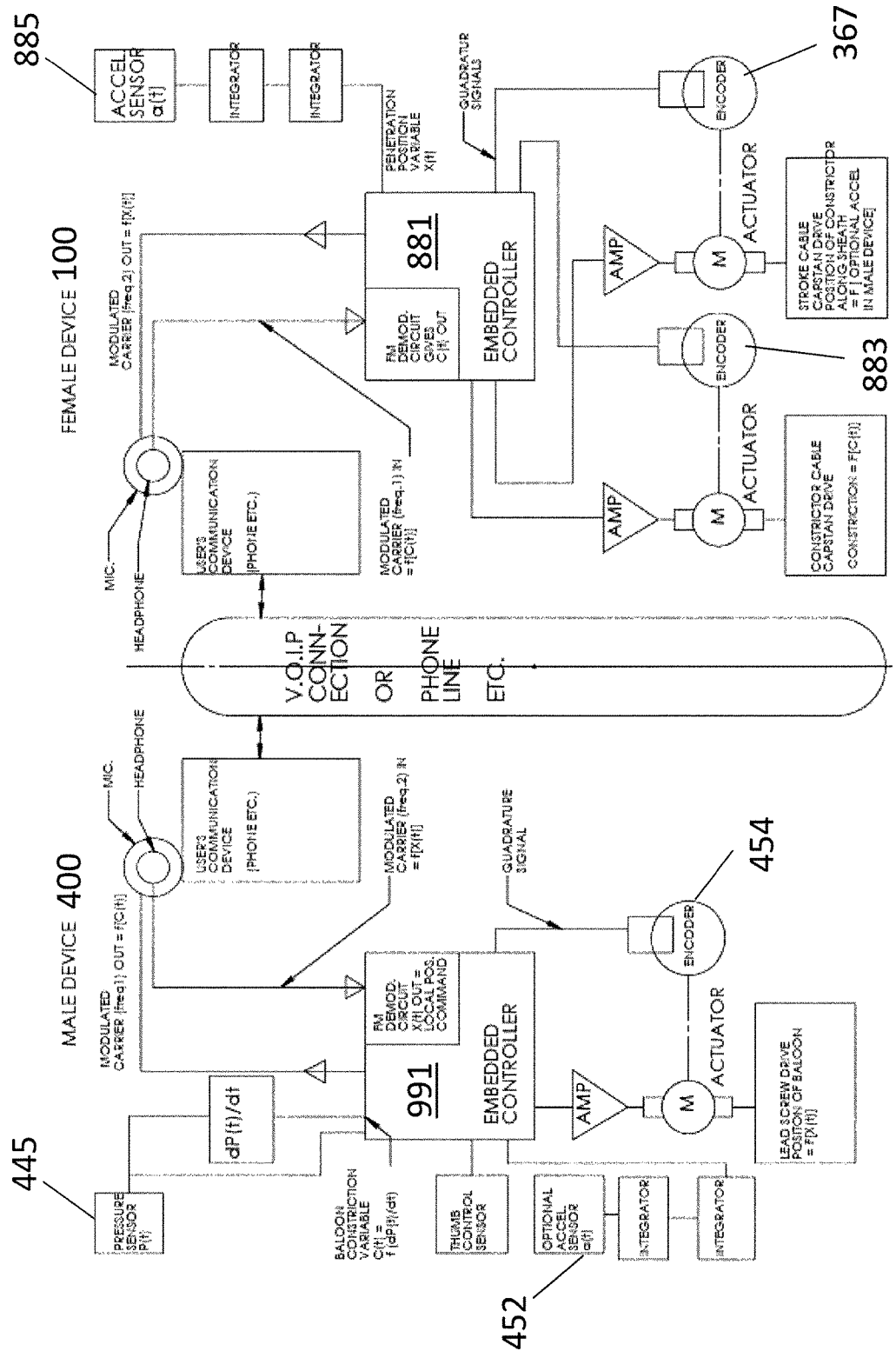
FIG. 17 is a system schematic of two paired sexual stimulation devices.

Referring to FIG. 17, the devices 100, 400 can be configured to communicate with one another. For example, the female device 100 can be configured to determine, through the sensor 885, the penetration position of a user into the device. This position can be communicated to a paired male device 400 to control the position of the ring 403 through encoder 454 and the controller 991. Simultaneously, the male device 400 can be configured to determine, through sensors 452 and 445, the penetration position of the device into a user and the pressure of the ring 403. The detected position and pressure can be communicated to the paired female device 100 to control the position and constriction of the ring 103 through encoders 367, 883 and controller 881. Thus, the devices 100, 400 can simultaneously transduce the experience the user would feel if their genitalia were actually engaged in copulation.

One exemplary control scheme includes:
1. Female device 100 directly measures penile penetration into the synthetic vaginal canal and encodes that into a telemetry packet or signal.
2. Female device 100 sends a penetration position control signal to male device 400.
3. Male device 400 receives penetration position control signal and servo controls inflatable balloon to commanded position real-time.
4. Male device 400 directly measures pressure of translating ring and encodes that pressure into a telemetry packet/signal comprising constriction pressure and position (if the male device 400 has a helically wrapped semi-conductive sensor strip 800, 900 incorporated into the sheath, then vaginal penetration can be measured directly).
5. Male device 400 sends vaginal constriction and penetration depth signals to FL device.
6. Female device 100 servos to penetration depth and servo controls constriction to replicate stroke and contraction of vagina.

The communication between the devices 100, 400 can be performed through audio signals with a nominal latency of less than 0.25 seconds over internet connection or telephonic connection. For example, as shown in FIG. 17, communication can be performed through an audio connection over a voice over internet protocol (VOIP) connection.

The devices 100, 400 can thus include or have connected thereto a tone generation and transmission mechanism, either in firmware or purely electronic, modulated by a control signal whereby a carrier base frequency is increased or decreased by a continuous range in response to the control input. For instance, a 6 KHz frequency generated in firmware, is modulated by adding a variable in firmware that can increase the signal frequency to 7 KHz in steps of one part in 255 in response to a pressure signal from a sensor being read via A/D convertor. This control signal can then be filtered, conditioned, AC coupled, and sent out to a common audio microphone jack. The microphone jack can be the point of interface where a frequency modulated control signal is input to any device with an audio jack connection capable of sending voice signals over a radio or land line connection. For instance, a hand held phone, tablet computer, lap top computer, may all listen to this control signal. When connected to a common VOIP program like Skype, any other device anywhere in the world can "hear" this signal and the original modulation from the telemetry generated at the remote local processor is faithfully maintained.

At the receiving end, any common device having a connection via Skype or telephone line, with a ubiquitous audio output headphone jack, sends an audio signal out of that port that is a faithful reproduction of the frequency modulated signal.

That FM control signal is passed through a filter, an amplifier, and then a carrier frequency detection and demodulation stage, where the original modulating signal is recovered and turned into an analog voltage with a bandwidth equal to the original sensor a the remote end. That demodulated control signal is then fed into the local processor via A/D convertor at the local receiving device end and recognized by firmware as a control signal for positioning a servo.

Telephony, either via analog connection or internet VOW connection, is typically constrained to a frequency range of 10 to 3400 Hz by very old telephone specifications. Ability to clearly understand speech benefits from frequency content up to 10 KHz. However, it is possible to remove a portion of the frequency range above about 5 KHz and minimally impact speech quality. The audio output that comes out of the audio jack can be intercepted and filtered with a low pass filter to filter out the modulated carrier frequency. That filtered signal drives a pair of headphones or powered speakers that can be connected to each device 100, 400.

Common electrical signal modulation schemes used alone or in combination, such as Frequency Shift Keying, Pulse Position Modulation, Amplitude Modulation, Frequency Modulation, Sideband Modulation, etc., can be used to send encoded bytes of sensor information and command signals back and forth simultaneously over the existing audio connections in common devices.

In the case where there is a single sensor and proportional actuator at each end of the network connection, approximately five to ten bytes of data can be sent to and from each end at an update rate of ten times per second. This design can require transferring up to 800 bits per second, which is well under the audio bandwidth capability for the common connection. To improve quality, CRC error checking can be implemented or redundant signals can be sent to ensure performance.

In some embodiments, a single controller can be used to control several actuators and respond to several audio input signal simultaneously.

In one embodiment, where there are two actuators to be controlled with one audio channel, the modulation range can be divided into a low and high band, and then the signals can be alternated based on which one is changing. For example, in the case of the male device 400, there is a pressure sensor and an accelerometer signal, so both can be monitored, and whichever one has changed the most in a given time interval will get to be updated. At the female device 100 end, the controller just knows to pay attention to whether it is a high or low modulation range and steer the signal to the appropriate servo control plant in firmware.

Advantageously, by using an audio connection to transmit signals between paired devices 100, 500, the communication is performed through a very high bandwidth, low noise, stable, connection that requires one to simply plug in a jack without software requirements.

Networking

In some embodiments, the connection between one or more devices 100, 400 can be made over a network that can relay or record sensor and actuator signals for: (1) later playback, e.g. favorite session, sexual greeting card; (2) broadcast, e.g. one performer to many sexually engaged observers; or (3) analysis, e.g. study of correlation between a devices' position sensor readings to "sexual effectiveness" sensors on the same patient, or to a remote device's "sexual effectiveness" readings for a given session/time period.

Figure 10:
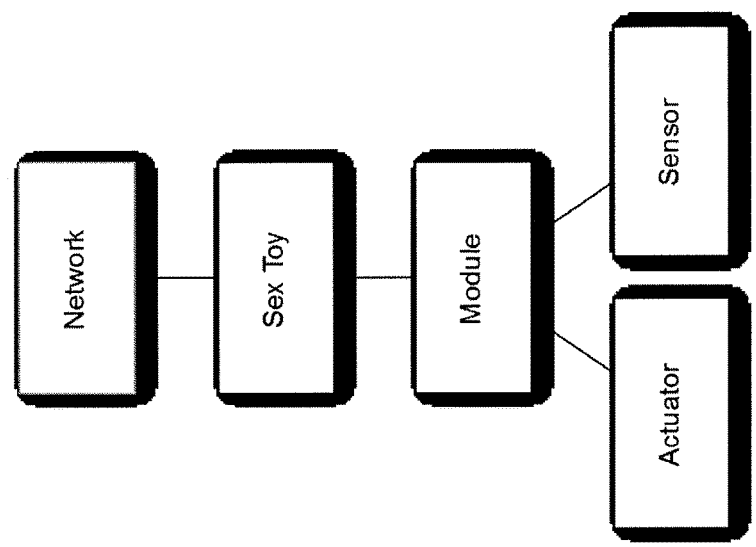
FIG. 10 is a diagram showing connections between a network, a sex toy, and the module, actuator, and sensor associated with the sex toy.

Referring to FIG. 10, the sexual experience obtained from a sex toy (or device 100, 400) can be shared on a network (sometimes referred to herein as KarmaNet for exemplary purposes) through transmission and activation via sensors on the devices. While the users interact with devices of sex toy form factor, the devices are connected through a network. The network can include, for example, a server, and a chat client.

Figure 15:
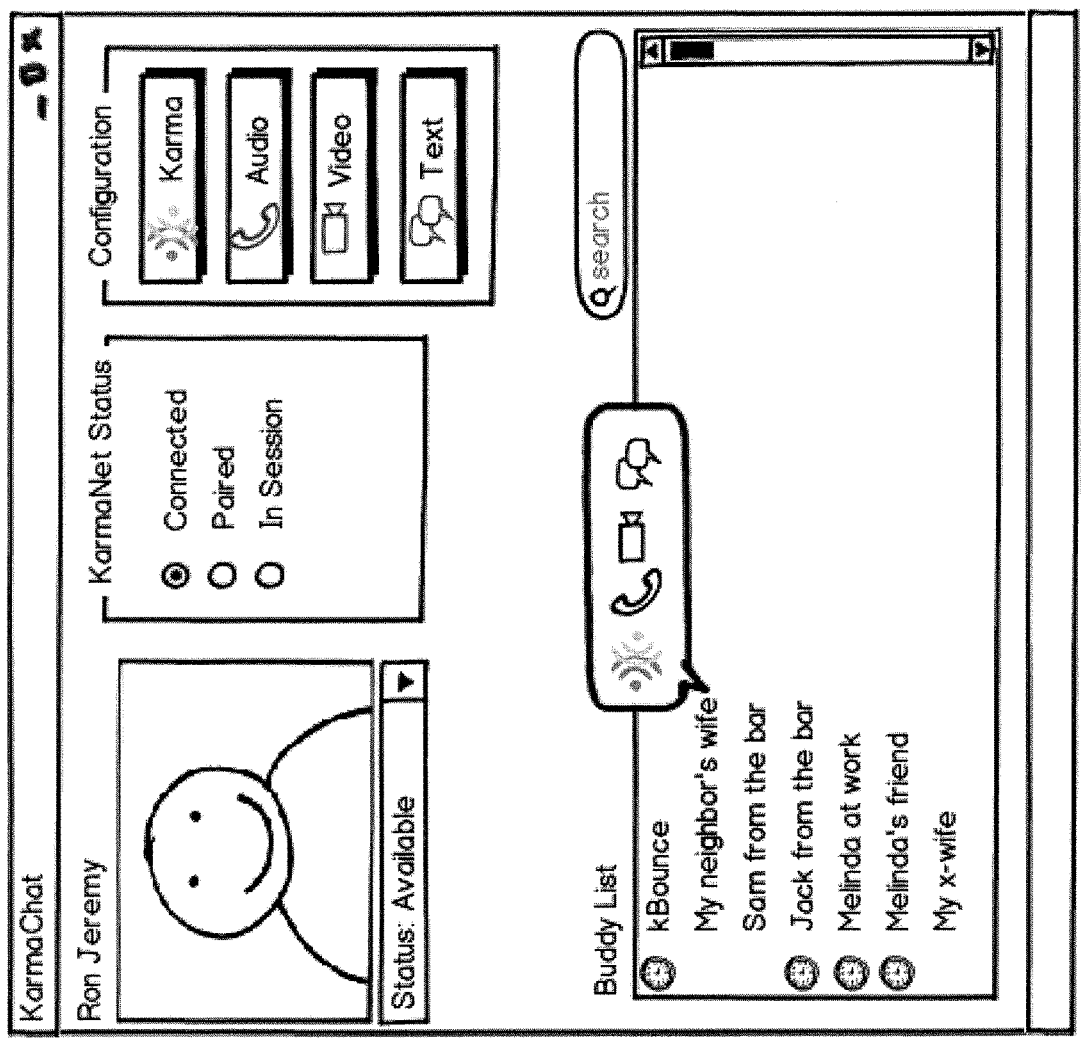
FIG. 15 shows an exemplary chat client for use with one or more sexual stimulation devices.

An exemplary chat client is shown in FIG. 15. The purpose of the chat client is twofold: extend the otherwise limited UI of the device, and provide a communication bridge to the server. The chat client can enable users to select from a buddy list and connect via audio, video, text chat. Further, the chat client can know how to find and pair with a device 100, 400. In the upper left of the chat client shown in FIG. 15, the user show as logged in (name appears) and has set his status for other buddies to see. In the upper center, the GUI shows the user as logged in to the server but with no device paired or recognized; once paired to his local sex toy device, this user would be able to enter a session. In the upper right, options for this user's chat modalities can be controlled. For instance, this is where the user would pair with his Karma device and set any controls. In the buddy list, available buddies show as identified by their public aliases. Public aliases may work much like hash tags on Twitter, perhaps always a "k" (for Karma) prefix. Or, the user who has logged in may ameliorate or replace the fairly anonymous public alias with a more descriptive nickname that shows only to him (it may not be unique, while the public alias is required to be unique because it identifies the user uniquely to other users). For each user, that user's online status is communicated to the left of the user's public alias (or nickname). Scroll over the online buddies to connect via Karma sex toy (leftmost icon). If a buddy is offline, this user's recorded sessions with that buddy may appear.

Several exemplary use cases are presented here for the purpose of explaining primary objectives for the network. These use cases do not intend to define the complete set of foreseeable network features. Rather, they are meant to identify a few core operations that drive fundamental design requirements and establish core intellectual property.

One exemplary use case is an account set-up use case (here, called a KarmaNet account). In the exemplary case, a woman connects to server via web browser. She generates login and password information which will remain private. She is then prompted to enter billing info, which is kept private as well. Lastly, the woman is asked to create a public alias for display to other users. If this woman happens to be a performer, she may later use this public alias to advertise herself.

Figure 13:
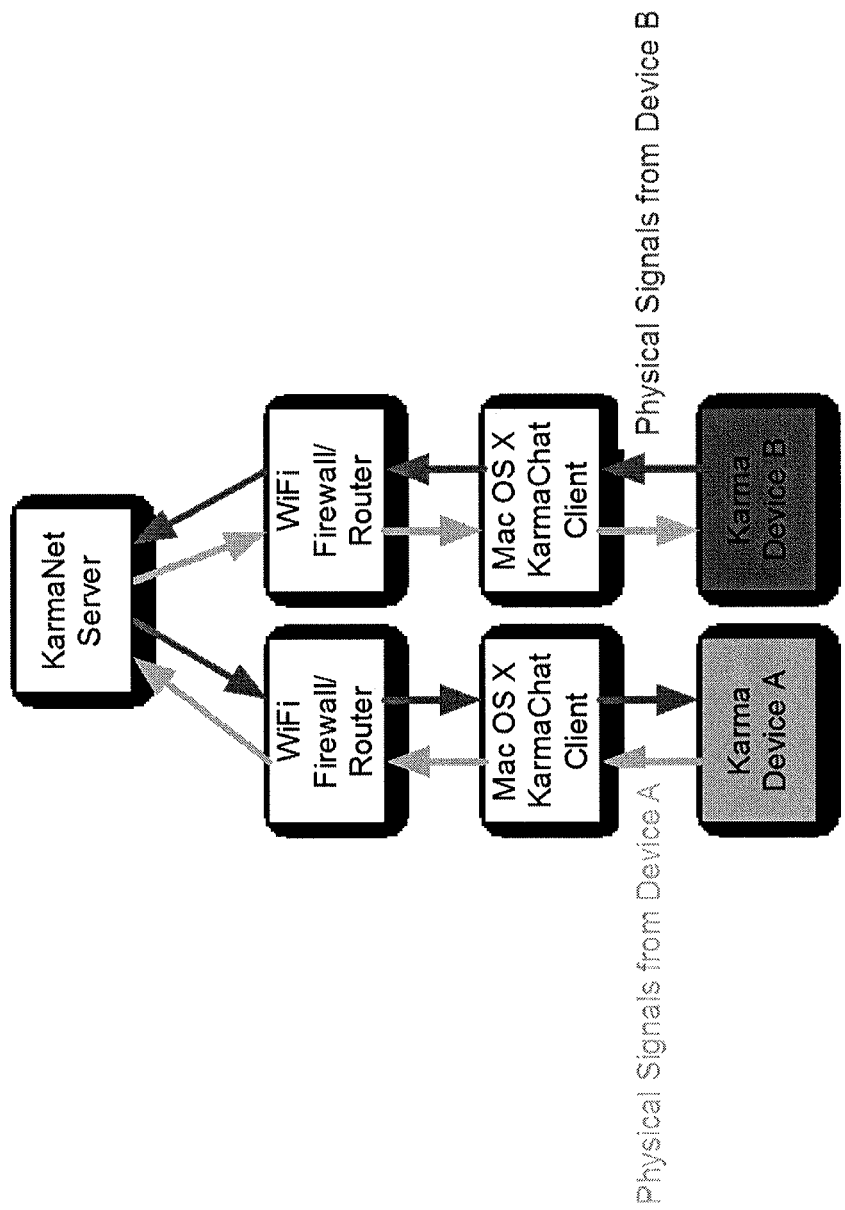
FIG. 13 is a diagram showing an exemplary peer-to-peer use of paired sexual stimulation devices.

Referring to FIG. 13, another exemplary use case is a peer-to-peer session use case. This use case represents the scenario, for example, in which a husband and wife engage with each other over the network. The husband in London hotel logs in to a chat session via browser or stand-alone app (PC or smart phone) with the intention of engaging his wife in their New York home. The husband turns on power to his/her sex toy or device 100, 400. Through the chat client, the husband sees his device name come up through the host/server. Husband pairs his chat client with the familiar device. He then looks through his buddy list, where he finds his wife's public alias. He can see from an icon to the left of her name that she her device is paired and ready. He starts a session with her, including video and KarmaNet connection, but not audio.

Figure 14:
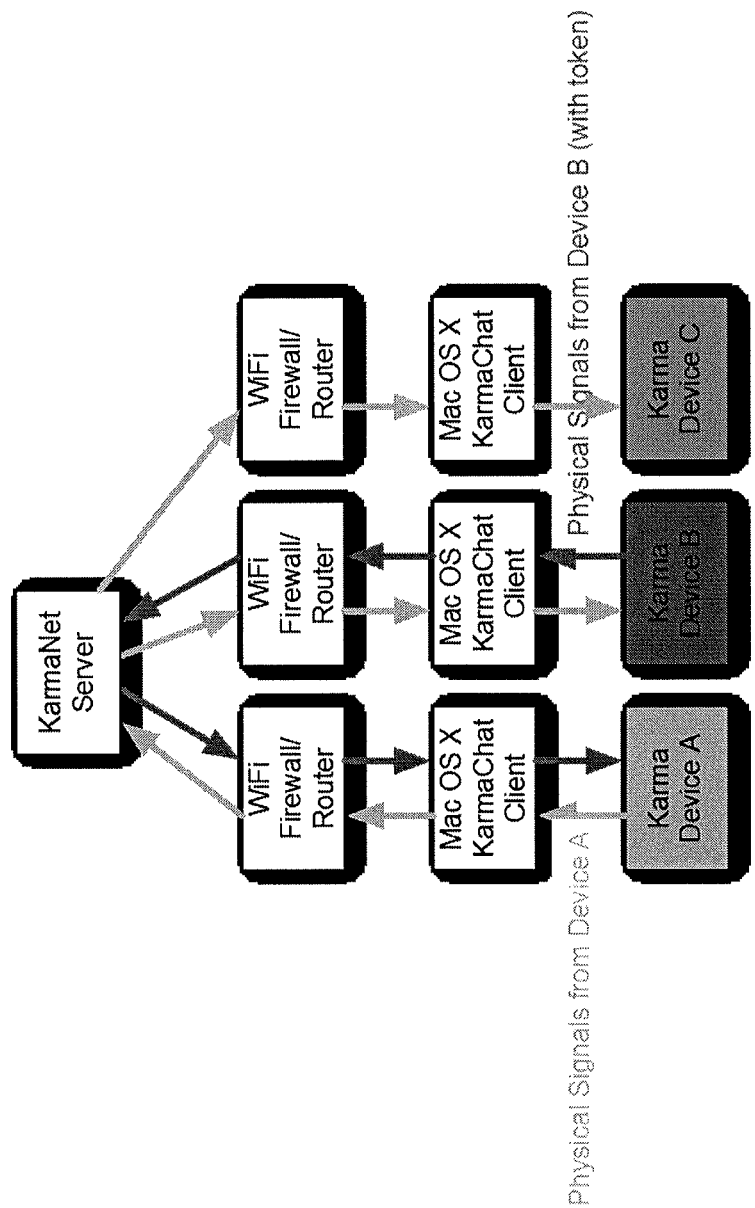
FIG. 14 is a diagram showing an exemplary performer broadcast use of networked sexual stimulation devices.

Referring to FIG. 14, another exemplary use case is a performer broadcast use case. For example, a female performer wishes to perform to a male audience. That performer may choose to engage with any one male member of her audience at a time. The males in the audience cannot see each other's public aliases, as in a chat room. But the female may see the full set of public aliases in the audience. For example, males Al and Bob see advertisements or reviews for a particular performer, "kBounce". Both Al and Bob, who don't know each other, type "kBounce" into their respective chat clients to add the "kBounce" public alias to their buddy lists. The performer logs in and pairs her device. Because the performer is listed in his buddy lists, Bob sees "kBounce" status as ready. Bob, the first audience member, clicks on "kBounce" to start a session. His device is coupled over the network with the performer's device. Al, Chris, and other audience members also join. Within Chris's chat session window, "kBounce" is listed under his public alias. So is "5 others". He sees by an icon that he has a slave device that plays what the perform broadcasts, but from that icon he knows that his device is not coupled back to her device. The performer elects to move the token in a random order through her audience list. Chris is ultimately selected, and the token moves to him. When he sees his icon illuminate to mean that he is the sole audience member coupled round-trip with the performer, he alters his input to try to please the performer.

As shown in FIG. 14, a performer with a device can thus broadcast his or her sensor readings to multiple remote observers with their devices, all in one chat room. Observers may be watching, listening, text-typing, and most importantly, engaging with their respective devices as those devices receive and play the sensor signals from the one performer's device. In the spirit of teleoperation, Device A's actuators can react to sensors signals from at least one of the other Device B or Device C. However, to avoid Device A's actuators playing a hodge-podge of noise conglomerating signals from the multiple attached devices, options for coupling Device A's actuators to reality are: (1) the performer using Device A elects not to have a partner while broadcasting, so Device A's actuators do not actuate (or perhaps they actuate per a recording); (2) the performer on Device A actively chooses among the connected devices, here Device B or Device C, is her partner. FIG. 14 shows the case where the performer has chosen Device B.

The performer can choose that software automatically scan through all the other devices that are actively receiving Device A's broadcast, sampling each Device for 10s of seconds (or any user-specified period) then on to the next, in true group sex fashion. This is akin to a "token ring", and the token is illustrated as if to temporarily belong to Device B. A pair of performers use Devices A and B, with corresponding male or female Devices C receive the signal generated. If the performer selects a single member of the broadcast recipient to be the active "partner", that unique broadcast recipient device can be made aware it's "got the mic" by a blinking light on its device or at the KarmaChat client UI. The active partner can choose whether to share audio or video back to the performer at the same time. In some embodiments, broadcast recipients may be able to communicate among each other much like in a chat room, if they concede to give up their privacy.)

Another exemplary use case is a play back recorded archive use case. This use case represents the scenario, for example, in which an unmarried man subscribes to a performer's recorded performance. Upon adding "kBounce" to his buddy list, Don sees that this performer is not online. But she is one of his favorite performers so he opens a window to choose one performance from her history of recorded performances. His icon illuminates as if he's in the audience but not coupled to the performer. The session continues as in the previous example.

Figure 11:
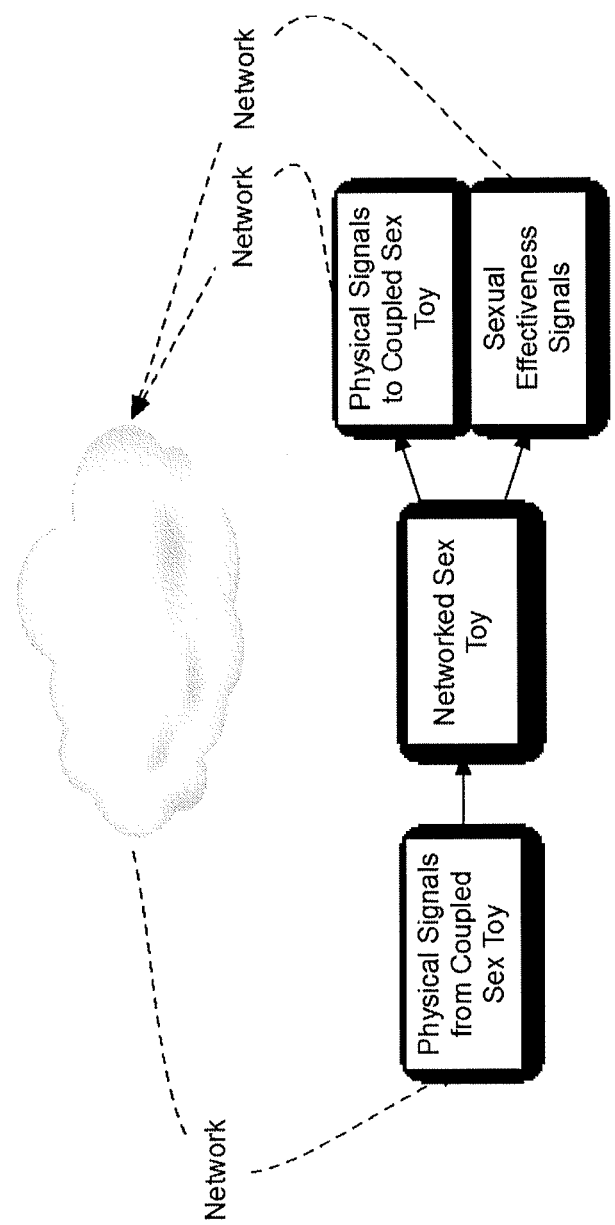
FIG. 11 is a diagram showing the transmission of signals to and from a networked sex toy.

Referring to FIG. 11, the transmitted sensed information can be either physical signals communicated between coupled devices on a network can be sexual effectiveness signals, which are used to evaluate a time history of physical signals with respect to its user, as described above.

One embodiment for connecting the devices 100, 400 to the host uses Bluetooth for its configuration simplicity; its simple pairing scheme would be advantageously familiar to anyone who's used a Bluetooth earpiece. Bluetooth is cost-compatible, with suitable bandwidth and range (depends on device class we pick, and a function of power consumption). In another embodiment, 802.11 (WiFi) can be used. Other connections include through ZigBee, proprietary RF, IR, visible light, audible tones, ultra- or infra-sonic signals, etc. Alternatively, wired solutions may be employed: serial, USB, Ethernet, FireWire, Thunderbolt, etc.

Figure 12:
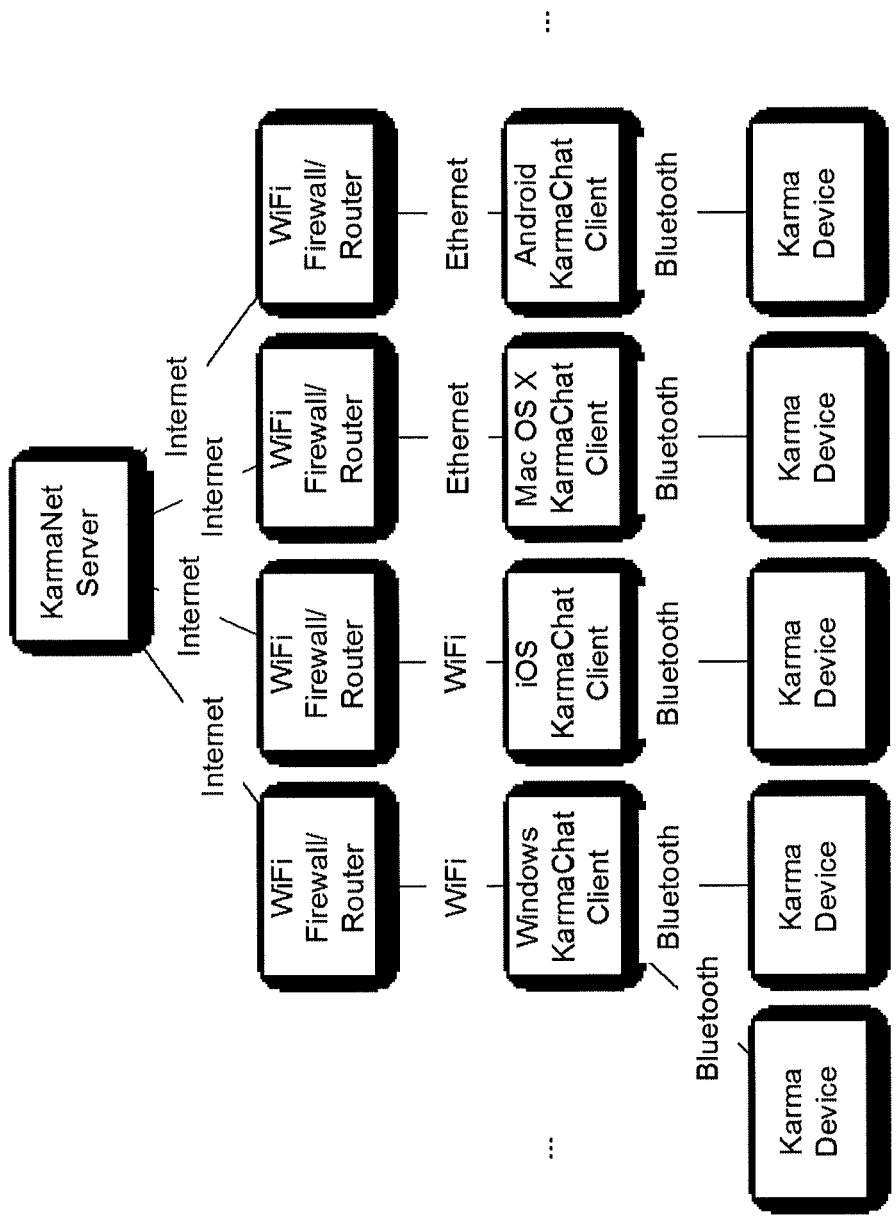
FIG. 12 is a diagram showing the components that provide sexual telepresence.

The purpose of the network is to enable teleoperation between two or more devices 100, 400 (or, one operating alone as it plays back a recorded session). Referring to FIG. 12, there are several components that ensure sexual telepresence, including multiple devices 100, 400 (here called karma devices), Bluetooth connections for each, a computer/telephone/connection device, Wi-Fi or the Ethernet, a router, the internet, and ultimately the host server. Note that while all of the identified devices are online at the same time, they are not necessarily partnered with each other.

In summary, a user may have in his/her home one or more sex toys, which he/she may connect to any host e.g. PC, laptop, smart phone, or tablet. The host runs KarmaNet proprietary software "chat client" (described below). This chat client knows how to pair with a Karma device over Bluetooth, and it knows how to connect to the KarmaNet servers over WiFi and Internet. In this way, the chat client is the bridge between a Karma sex toy device and the server. Teleoperation data, such as sensor signals, can then be relayed in real-time between two or more devices via two or more of these bridges. The partner device receives sensor signals and responds by affecting its actuators. Its actuators stimulate the user's anatomy, and the partner user's anatomy responds. That response, in turn, is sensed and fed over the same mechanism back to the first device. In this way the teleoperation loop is closed. Text chat, video, and/or audio may also be shared in addition to the teleoperation signals, just as in a regular chat scenario. In an alternate embodiment, the server may be cut out of the loop for efficiency, done by allowing chat clients to negotiate a direct peer-to-peer connection.

Typical loop closure rates of the teleoperation loop can be in the ~10 Hz range in production, though latency is as important as rate closure in determining stability. It is possible to detect latency and dynamically slow or speed up the loop closure rate. It may also be important to retain a recently buffered signal if the connection drops; the buffered signal will play as a loop until the connection is re-established (in sync with the loop signal), or the recently buffered signal will slowly fade away if the connection isn't restarted after several (~5) seconds.

For signals transferred between devices, one embodiment includes isochronous communication protocols. Streaming audio and video are examples of data that is isochronous, data that is refreshed regularly and is better to keep on playing even if a packet is lost (transient glitch). File exchange is a counter example, where all the packets must come across perfectly. If the option is available, it may be wise to use UDP instead of the more familiar TCP. UDP does not guarantee the arrival of signals. The protocol described herein can tolerate lost signals the same way real-time audio or video stream can (up to a point, then the device output fades to 'off' to avoid confusion on user's part, or to avoid instability). UDP is preferential because of its more "isochronous" nature~lower latency, lower packet overhead-~versus the more common TCP/IP standard. But, we are not constrained to use UDP.

In order to connect a device to the chat client, the chat client needs to be able to see the devices that are out there (once they are paired to the local host, the same way you pair a Bluetooth headset). Zero configuration networking solutions, like Bonjour, are typically used to advertise a device's services. Bonjour could be implemented in the sex toy firmware to allow the paired sex toy device to advertise its service, likely a UDP port. As a reference, there are online examples for how to run Bonjour on Arduino. When the sex toy uses Bonjour to advertise itself, the chat client may discover the sex toy and identify it as a Karma sex toy. The chat client would then check for the unique ID and pass it on to the server, where that unique ID may be required to negotiate/complete the connection. This way, the unique ID is used to maintain quality and protect the revenue stream by keeping Karma devices from being copied with knock-offs (note the unique ID should be encrypted in the sex toy device's flash, but the server can also do clever things to ensure that the same ID is used by the same user login).

Separately, the chat client must connect securely to the KarmaNet servers. It is common for a chat solution to leverage the XMPP standard (formerly Jabber). Google Talk is an example of an XMPP compatible client, and there are hundreds of other examples that run on all different OSs. Google Talk, for instance, provides voice, video, text, and file sharing capabilities among chat buddies. We anticipate that our chat client would be XMPP compatible, and would be implemented in a way that instances of the Karma chat client would talk only to the proprietary KarmaNet servers. Of course, our chat client would provide the additional capability to communicate physical signals and sexual effectiveness signals over UDP as provided by an appropriate XMPP extension, such as XEP-0166.

Another advantage to using the XMPP protocol is that several XMPP server codebases are readily available. The intention is that the KarmaNet servers run one of these XMPP servers, so the chat clients have something to talk to. Chat clients will be configured to look for Karma's XMPP servers, and only Karma's (as opposed to, say, Google's XMPP servers to which Google Talk clients speak).

The server can be responsible for working like a switchboard to connect the real-time sessions between, potentially, thousands of simultaneous users. Server features, perhaps distributed across multiple machines in the cloud, may include: (1) XMPP server which allows buddies to find and connect, as well as to search and add via public alias; (2) some implementation of the right XMPP extension to exchange real-time teledildonics traffic; (3) recording and playback engines, which build on the above XMPP component and have their own database; (4) database to track user data, including login and password, billing info, usage metrics, public alias, user association with a device unique ID, etc.; (5) usage engine, tracking usage and entering into database; (6) billing engine, to pull from database and bill users. Front end may be required, depending on ultimate business model; (7) mapping engine, to negotiate and push maps to KarmaChat software; and/or (8) analysis engine, to track usage metrics, etc.

Physical signals may be transmitted over the network in a few different ways including parametrically, such as position as function of time or individually, sensor by sensor.

The sensor-by-sensor is the more pure teleoperation scenario. The parametric technique is more bandwidth efficient and more likely to give stable, persistent performance through dropouts. Firmware would be responsible for fitting data to a function, such as a cyclical function like sine. Then, firmware would interpolate between updates as new parameters A and phi come in while t advances, such as in p=A*sin(t+phi). Depending on its location within the sex toy, each actuator would respond according to this function but with a different phase (add to phi).

One challenge with tele-operated devices is that they can be driven unstable when actuators and sensors are collocated. Consider the scenario in which one sex toy device senses it is being squeezed. It sends this physical signal across the network to the partner device. The partner device's corresponding actuator responds by contracting in order to match the sensed squeeze. Now, there is a sensor mounted to the partner device's actuator. When the actuator squeezes, the partner device sends a squeeze signal back to the original device. The original device squeeze more, in response, or less depending on the mechanical time constant and connection latencies. The result is what looks like noise, possibly with positive feedback heading toward instability.

Figure 16:
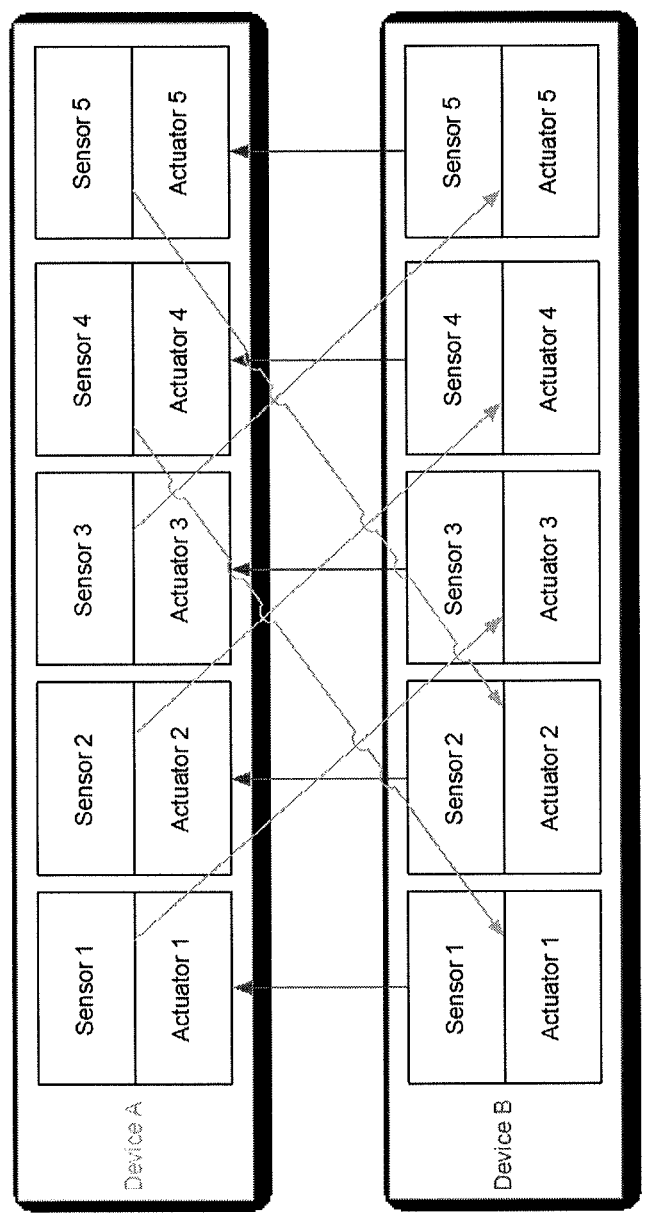
FIG. 16 is a diagram showing mapping between physical sensors on paired sexual stimulation devices.

Referring to FIG. 16, one solution to this undesirable scenario is to offer a mapping between physical sensors on the two devices, so that a sensor in an actuator/sensor pair does not stimulate the mirrored actuator on the partner device. The offset strategy, as illustrated in the figure below, breaks the collocation (assuming no coupled motion between, say, sensor 3 and actuator 5). This scenario is possible because physical update between a man and a woman partner can be convincing even if not exactly in phase.

It may be that Karma sex toy devices are simply not always symmetrical (i.e. different number of sensors and actuators, in different arrangements) between two coupled devices, so a mapping must be negotiated at the start of a session. The file that explains this mapping can live in firmware, as part of the chat client to implement, or on the server.

It is instinctive for males to compete for sex, and perhaps to compete at sex. In some embodiments, therefore, the systems and devices described herein can be used for gaming. In a 1-to-1 scenario, and especially in the 1-to-many situation when 1 broadcast recipient is temporarily selected as the performer's partner, there is a game to be realized. Upon getting his 30 seconds of fame, a temporary partner's goal may be to manipulate his own device in attempt to optimally stimulate the performer—to "perform back".

This "audience participation" is awarded a score by the server, score issued as a function of a) how stimulated the performer was in turn, or b) what the user generated with respect to what the performer is historically known to like. The server (discussed elsewhere) has the capability to analyze signals much the same way Pandora knows what music a person likes (but done through sensors instead of whether one presses the 'thumbs up/down' button).

Just as individuals seek compatible mates online, profiles of toy users, their preferences for interaction, movement styles, session durations or gender preferences can be used to recommend player liaisons. This match-making process yields opportunities for optimized connections among users and can be linked with profiles of third-party match-making services.

Sessions may be monitored, recorded, and analyzed by a server, such as for: (1) straightforward example of recording a session with one's partner, for when he/she is not available to engage real-time; (2) recorded sessions from professional performers; (3) sexual "greeting card", a recorded session from one user that is transmitted to another for playback at the 2nd user's convenience; or (4) for analysis, such as average anatomical size across a population. Pertinent for diagnostic medical device, behavior of a particular user, such as how often engages in sex (times per week), how hard and fast are motions during sex (over both time and frequency), time from first engagement to orgasm (for medical study of premature ejaculation), instances of multiple orgasms, transfer function(s) between physical signals and sexual effectiveness signals, correlation studies between sensor signals, including the orgasm button, rating or scoring sessions for extent of stimulation achieved, crowd-sourcing optimal sessions using machine learning and artificial intelligence techniques, optimizing configuration of a device or multi-device mapping, feedback from biometric sensors, or from the orgasm button, measuring progress during treatment of sexual dysfunction in men or women, or providing strategic "inputs", perhaps learned from crowd sourcing or designed by physicians/researchers, during treatment of sexual dysfunction.

In some embodiments, in order to monetize the connection, the internal firmware in each device can receive a token or cypher and then process it via another piece of online software. This can allow a service provider to charge for the connection and still allow the user to use the free audio method of connection. The token can be purchased, for example, and then a signal downloaded through the same audio connection without any more effort from the user that simply going to our separate site, and selling time. A cypher can then be uploaded into the device.

Additional Embodiments

Figure 18A:
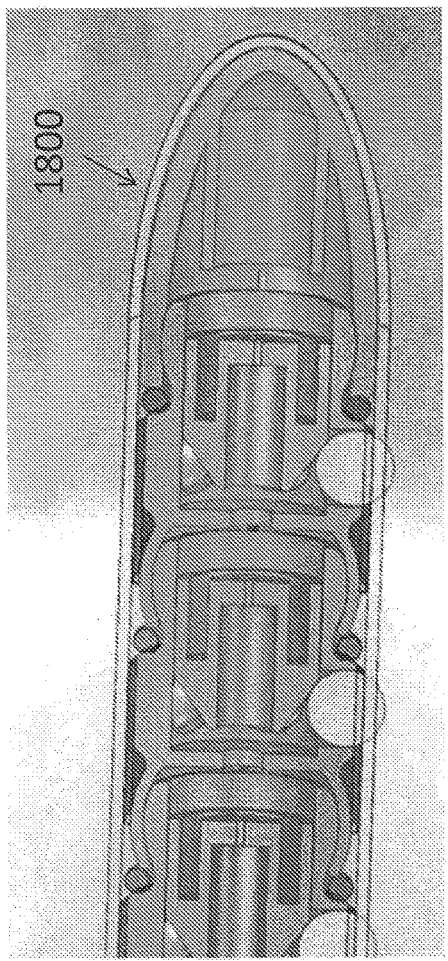
FIGS. 18A and 18B show another exemplary embodiment of a sexual stimulation device.
Figure 18B:
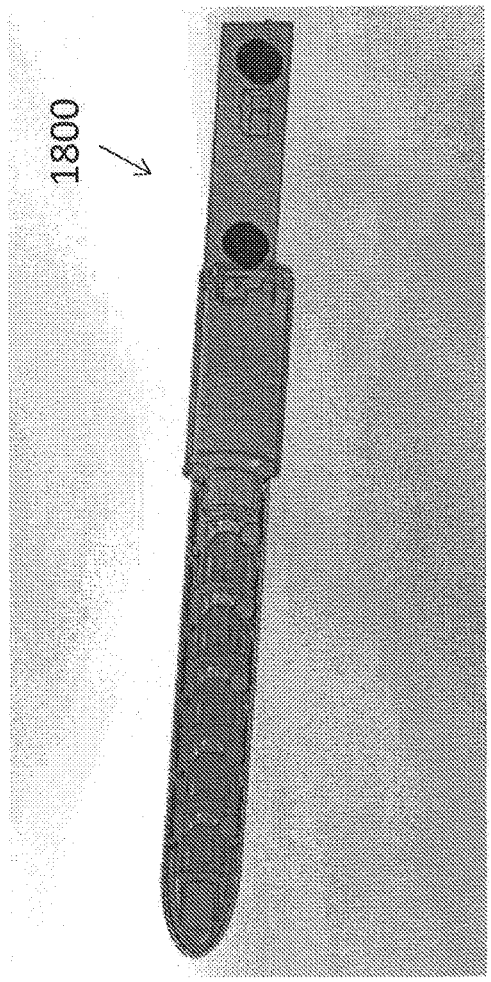

Referring to FIGS. 18A-18B, an exemplary multi-segmented penetrative sex toy 1800 includes individually actuated expander mechanisms and a co-located flexible sensor capable of measuring subtle and large deformations as the device is inserted into orifices, stroked, or touched in any way. The segments are rotatably coupled by way of ball and socket features in each segment and there is an elastic element disposed between each segment to provide restoring forces to a neutral—straight—position. In each segment, multiple balls are acted upon by a conical plunger that is actuated in tension by a fine cable. The cable is tensioned by an SMA element controlled by a micro-controller providing PWM excitation. SMA elements are arranged in a pulley rack in the device handle. A living hinge spring beam part provides bias force to restore the SMA wires. In addition, the outer sheath also provided restoring force.

Each segment is capable, under microprocessor control, of reporting an instantaneous constrictive and expansive strain signal with no limitation in bandwidth (up to hundreds of Hz) due to the instant resistive response of the sensors. The diameter of the assembly can grow, for example, from a 28 mm girth to ~40 mm when fully actuated. Each segment can actuate to expand out and generate expansion forces. While sensors are collocated with actuators, it is possible for the local position control of one actuator to be responsive to the strain measured on an adjacent sensor. This may be advantageous for control stability reasons when trying to replicate the forces on a tele-operated networked device it is paired to. In this case the Nth actuator may be controlled by the error signal of the paired device's Nth sensor, but be locally controlled by an error signal to an adjacent sensor.

In some embodiments, there are cables that attach to the conical drive plungers, they attach to beams with living hinges in the actuator housing. Those beams attach to SMA wire that makes two wraps around 15 mm pulleys. This SMA can be, for example, a 0.008 diameter wire with 11.6 ohm impedance.

All the SMA can live in a compartment that has forced air cooling. There can be a chamber between the pulley section and the segments for batteries, etc. There can be a cover over the handle end.

There can be five separate independent cable/SMA circuits where each conical drive plunger is independently actuated. Each plunger has two compression springs that bias it in its respective bore. This keeps the balls pressed out to approximately half of the actuator stroke. The reason for this is to create a nominal stretch on the sensor and have some range of compression for sensing. When the balls are driven out of the bores in the segments, they press out and stretch the sensor assemblies. The sensor can be, for example, a lamination of 0.010 inch thick silicone and the special semi-conductive material. The resistance drops as the balls strain out and increases as they are pressed into the bores.

The restoring force for the SMA wires comes from the combination of the bias springs that keep the balls in a half out state and the stiffness of the living hinge beams in the actuator housing. Ultimately, forces put on the balls by the user will recover the SMA. There is no provision for a sensor to sense when the 400 mm of SMA wire has contracted to the full 8 mm required to move the plunger all the way.

The actuator housing and the beams with living hinges are where wire strain can be sensed. This can be as simple as a contact that is made between any beam and a common electrode. Firmware can ensure that the devices doesn't exceed 2% strain and/or overheat the wire.

In one embodiment, the actuators will expand the outer girth from 29 to 39 mm with about one pound of total radial force divided by five balls on each segment. The rubber sensor ring will tend to spread out force and strain so individual balls will not be felt through the sheath (although that may be interesting).

Each conical drive plunger can be perforated with holes permitting the passage of upstream tension cables and wires from the sensors. Each segment can be rotatable with respect to its adjacent segments and there is a low durometer o-ring between each segment to provide restoring force. The actuator common ground is at the terminal block in between the pulleys. Each flexure beam has a separate wire that goes to the Mosfets. Thus, for the actuators, there are six wires that need to carry up to an amp. Each sensor assembly has two fine electrodes coming from it. They will live under the sheath and do not enter the mechanical assembly. There is a provision in the tip part for an ERM for vibe. The very proximal end of the device incorporates a quiet, compact, fan. This would draw air past the SMA spools.

Figure 19B:
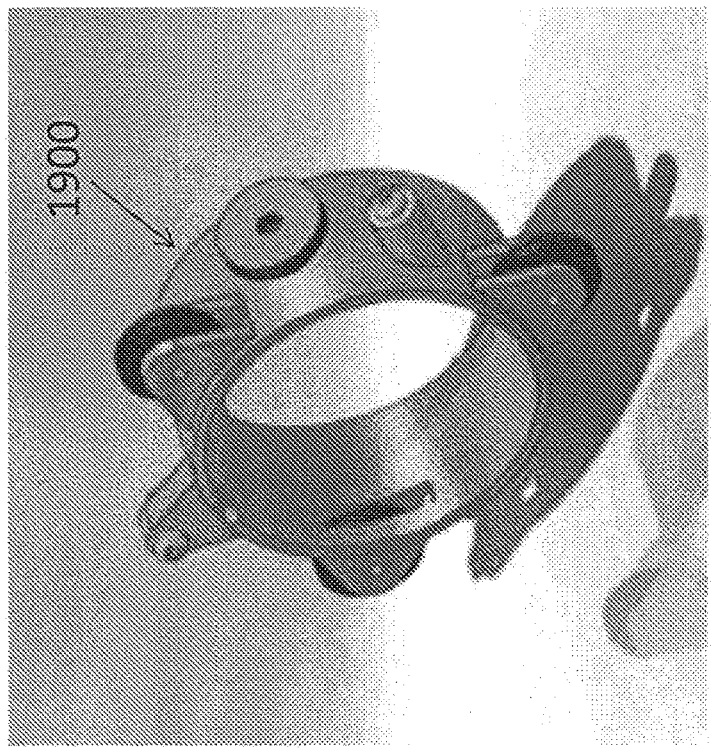
FIGS. 19A-19D show another exemplary embodiment of a sexual stimulation device.
Figure 19A:
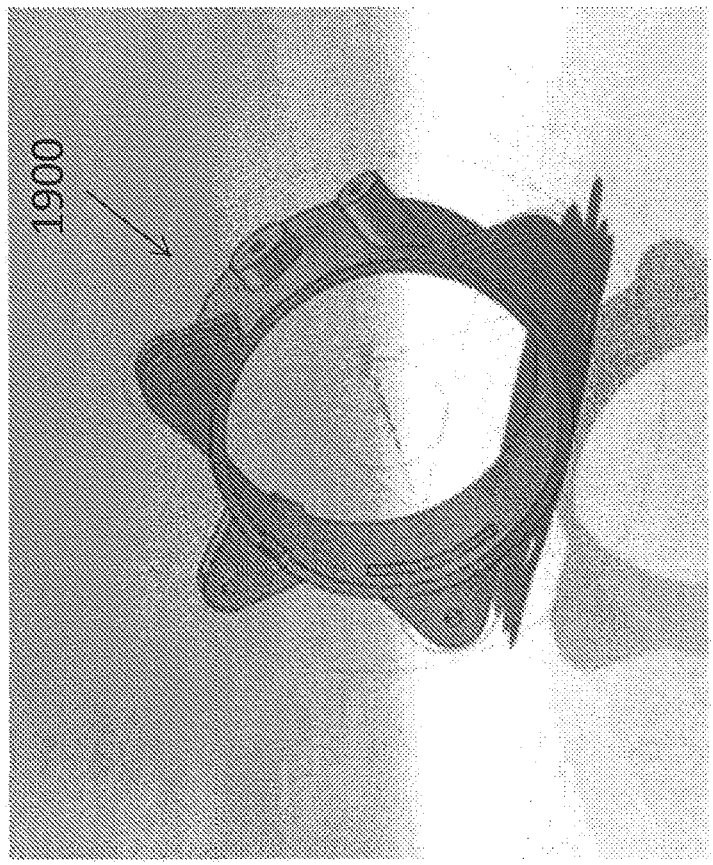
Figure 19C:
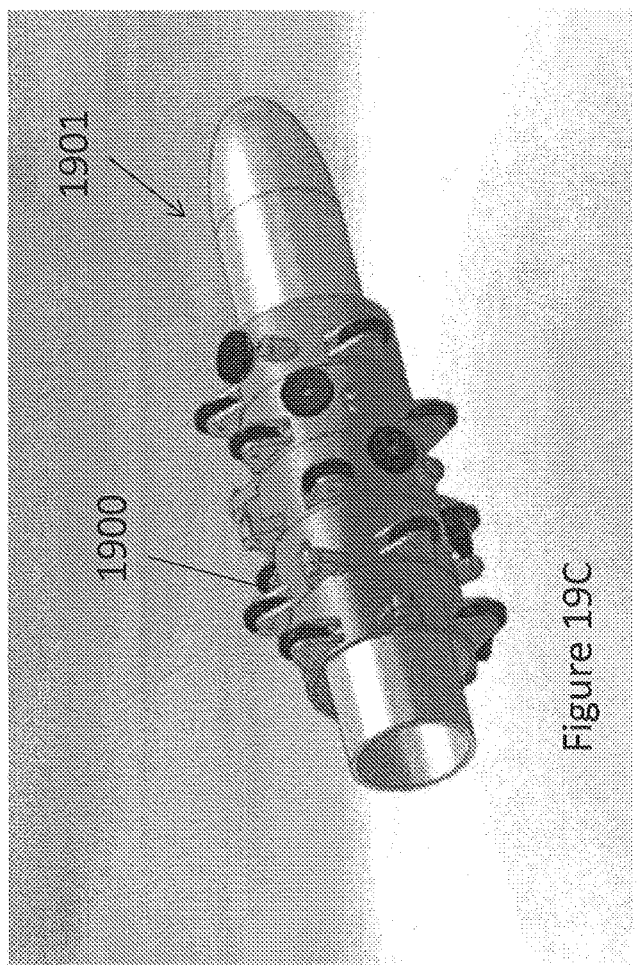
Figure 19D:
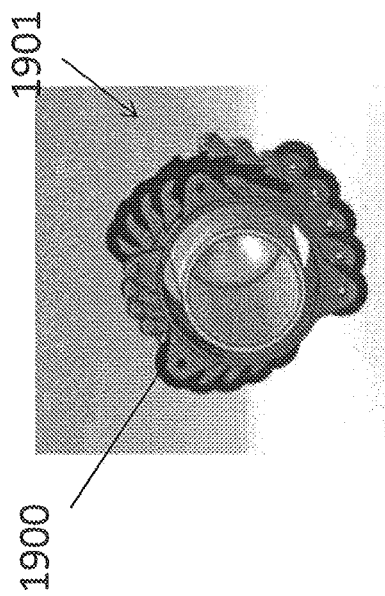

Referring to FIGS. 19A-19D, an actuator 1900 can be configured to be incorporated into a male masturbator device 1901. As shown in FIGS. 19C-19D, series of these actuators 1900 can be arranged in a larger assembly such that they all act independently on a soft elastomeric vaginal canal insert.

A penis inserted into the sleeve will sense a range of subtle to forceful contractions of the canal by effect of a cable that circumscribes the canal's outer surface with three tangent contact arcs. As the cable is tensioned by SMA actuators (or alternative actuators), the sleeve is compressed against the tissue of the penis. Alternate actuators could be DC motors with cable winding capstans or gear train drive. Additionally, solenoids, or electromagnetic variable reluctance actuators could be used.

The tension cable, is terminated to the plastic section part and winds around three pulleys before turning on a fourth pulley where the cable then runs parallel to the cylindrical axis of the toy. Just after this pulley, the cable is crimped or otherwise joined to a length of SMA wire. At the distal end of the toy (away from the simulated vaginal or anal opening), there is another pulley on a translatable ring that is concentric to the axis of the canal. The SMA wire wraps around this translating pulley and returns to a fixed termination on the same plastic section or a neighboring plastic section. Electrical connections to the SMA wire are made at these terminations and the crimp between the SMA and the cable.

As the SMA contracts, the tension on the three sections of cable between the pulleys applies compressive forces to the elastomer insert resulting in its contraction around the penis. Each actuator segment is independently controlled by a microprocessor.

The translating ring is adjusted by an external knob on a thread (not shown) or some other means to adjust the effective preload on the cable system. This way, the vaginal opening diameter, tightness, is adjustable and the effective constriction on the penis is variable. It is important to note that the SMA will provide the same 2-3% contraction on the cable system regardless of the pretension by movement of the sliding ring, therefore a wide range of penis girth will be accommodated by the device and the relative intensity can be adjusted with this one simple mechanical control prior and during play.

The soft elastomeric sheath may incorporate one or more sensors. One or more soft elastomeric semi-conducting sensors as described in this document may be attached to the silicone sheath's outer surface or otherwise embedded into is as molded to provide a varying electrical signal in response to the motion of a penis inside the canal.

Either a series of sensor bands or a single strip with multiple electrodes would likely be attached or molded into the sheath. Ideally, each segment of the actuator would have a corresponding strain sensor.

Thus, in the embodiment of FIGS. 19A-19D, all cables are tensioned by a single control knob that sets the slack in the system and applies an adjustable preload. There may be a series extension spring in the cable path as well as a spring to keep the SMA on the pulley under all conditions. The latter spring would be of negligible impact on constriction force while the former would need to be stiff to allow transmission of SMA contractile forces. Cable and pulley subassemblies are compact and are capable of fitting in the empty space between the synthetic flesh sheath and the outer shell of commercial masturbator sleeves. Use of one or more flexible sensors on or molded into the soft fleshy sheath internal to the actuator assembly. Independent control of constriction cable pre-tension allows the user to adjust bias force (the constant amount of constriction) without changing the force or the displacement of the SMA actuation. Therefore, a range of penis size will experience the same sensations regardless of girth. This not only equalizes pleasure for the user, but also enables the tele-present participant to enjoy a larger signal from a tighter fit. This in combination with user adjustable control of the SMA "volume" or output power, will allow a very wide dynamic range of sensitivity. To provide variable preconstruction of the canal (or for expanding the girth of a phallic device), one or more fluid passages can connect reservoir with a check valve and pump region to distally located inflatable regions molded into the soft tissue. By pumping the pump, the passages pressurize the chambers with fluid or air casing internal or external swelling. A release valve would provide release of pressure.

In some embodiments, a constricting actuator can include a plastic arc with helical grooves machined in it before the slot is cut. Two screw terminations can provide anchoring and connection to SMA wire which is wrapped in such a way that it crosses over the gap in the ring. When current is passed through the SMA, the ring contracts forcefully changing its inside diameter noticeably. Inserting a finger into this 25 mm ID, one feels large forces in response to a changing electrical signal. PTFE tubing can be used to minimize the friction of the wire on the groove. This increases recovery time between actuation pulses, but also increases mechanical efficiency. Several wraps can be used to achieve a long life with a sizeable elongation at only 2% contraction.

Figure 20B:
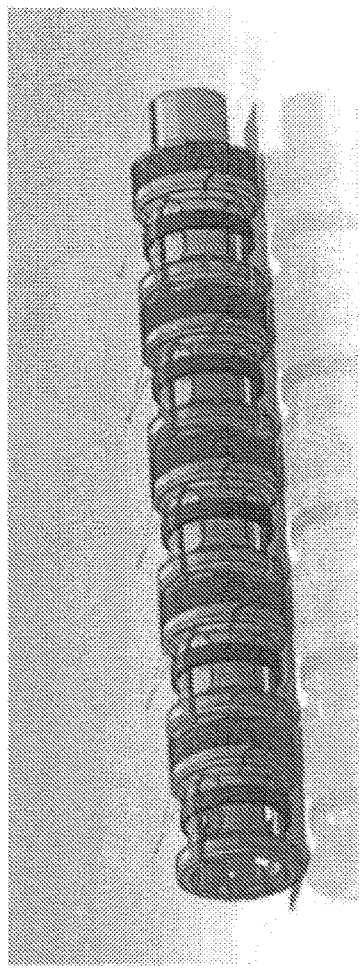
FIGS. 20A-20C show another exemplary embodiment of a sexual stimulation device.
Figure 20C:
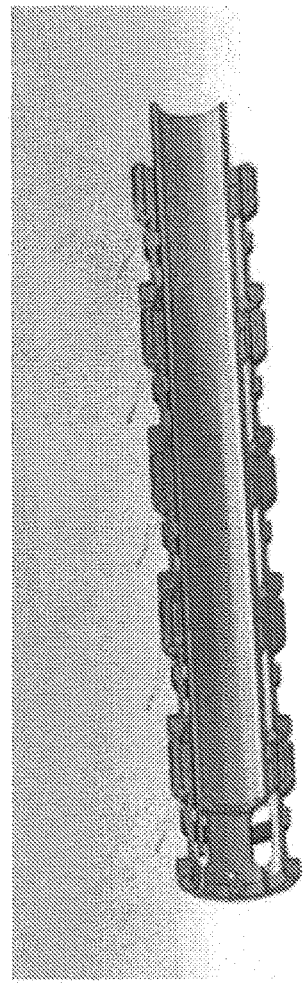
Figure 20A:
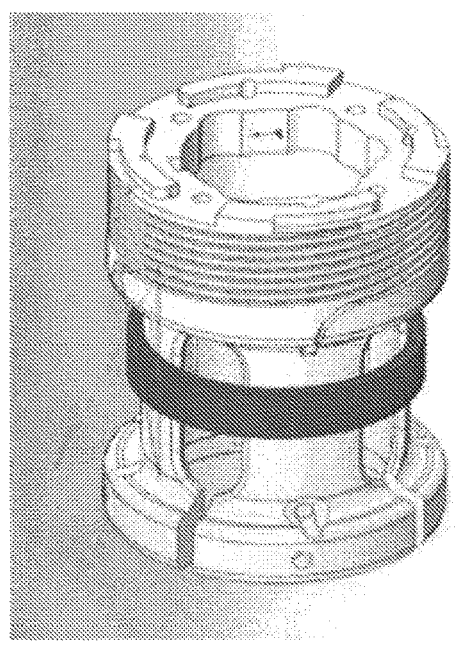

Referring to FIGS. 20A-20C, an actuator device 2000 can operate within the "just noticeable difference" (JND), i.e., the minimum distance between two stimulators interacting with skin on various parts of the body having different sensitivies, or the differential strain on tissue between two stimulators, of genital tissue. The actuator device can include at least 16 independent realistic contraction/expansion actuators with the same number of independent force/displacement sensors.

In order to achieve long actuator life (<500,000) cycles, the materials for the actuator device can be operated at <2% strain. In order to have an array of say, 16 actuators along and around a 180 mm long phallus device or inside a 180 mm deep vaginal canal device, the device can include approximately 200 mm of wire for each actuator.

Further, real genital internal displacements and contractions are on the order of 0-15 mm during intercourse or orgasm. Just the natural compliance of tissue is in this range and in order to sense position and provide actuator force over this range, the actuators in the actuator device can each comply over such a distance while sensing their position and being able to exert forces under command of the remote device.

A 1% strain on a 180 mm SMA wire will produce 1.8 mm of contraction. This is at least ⅕ of the requirement. We need some mechanism that not only packages the wire efficiently, but at the same time amplifies the displacement to approach 10 mm. With such amplification, a nominal 30 mm diameter phallic toy could expand any of its 16 actuators to increase diameter realistically or raise several in a row in response to real stroking at the other end of the tele-robotic link. Conversely, a vaginal toy could contract from 30 mm to 20 in diameter with very realistic force levels during orgasm. Keep in mind that all of these actuator-sensor pairs are independent and transducing what they feel while at the same time exerting what the other coupled device senses in real time.

For purposes of simplicity, FIGS. 20A-20C show only the female version (i.e., mimicking female anatomy) of this concept. The male version would be similar, but inverted mechanically.

The central element of the design is a battery housing tube that provides a semirigid housing for three NiMh battery cells. Five segments are located on the housing and aligned by an anti-rotation feature molded into the housing.

Each segment has four (and could have more) separate living hinge cantilever beam elements. There can be approximately 20 mm distance from the end of the beam to the body of the segment.

The first problem the segment design solves is displacement. Each beam element can be deflected approximately 10 mm from its resting state or compressed 3 mm inward. The bottom of the beam is at least 3 mm below the outer diameter of the segment (which is 28 mm, a practical diameter considering over molding silicone and comfortable insertion for anal sex). In some embodiments, this 3 mm difference is critical. There is a triangle formed between the top of the segment and the end of the beam. If we span this distance with a length of SMA, and contract it by 1.8 mm, our beam will forcefully move 10 mm. This actuator beam geometry effectively amplifies displacement.

The next problem the segment design solves is how to house 180 mm lengths of SMA wire. We have four elements to actuate and house independently. They must be mechanically terminated and insulated electrically. There seemed no practical way to simply extend the wires past the beams as this would result in a very long toy (at least 180 mm longer than we want) and rigid elements would need to be reacting each wires tension. This would be a packaging mess.

A volume efficient innovation is to wind the wire in a helix around the outer diameter of the segment. A helical groove provides a nest for the wire. Further, four separate thread starts can house four wires in the same length as one.

Each wire is terminated at the end of its cantilever beam and at the proximal end of the segment. Conventional stranded conductors carry electrical signals to the SMA wires. The problem with this helical configuration is that the wires are operating on a capstan effectively. This means that the friction forces opposing the wires contraction are exponentially increasing with the angle of wrap. We are making almost two turns of wrap and this would significantly reduce the available force. Another innovation is to sheath each wire in PTFE tubing in each helical groove. This reduces the operating friction to a negligible level. While such a sleeve will reduce heat transfer and slow down the rate of contraction, we expect that a real transduction system only needs 10 Hz of bandwidth and thermally conductive fluid like deionized H2O could be used to boost bandwidth if required.

In some embodiments, a cylindrical sensor band (similar to the sensors described above) is wrapped around each of the segments. Each beam must deform the band in order to expand or contract. Each beam has several electrode wires that make contact with the band. The band is a compliant structure comprised of two layers: a thin silicone rubber sheet on the outside and a layer of electrically semi-conductive elastomer material on the inside. Any displacement of the beams will change the resistance between one electrode on one beam and another on the moving beam. Each beam has a unique set of electrode pairs that "read" the resistance of the portion of the single elastomer band in real time an convey that information to the A/D converter on the embedded microcontroller chip. This innovative sensor is elegant in that it is simply one band or a special lamination in contact with eight wires. Those wires could be reduced to printed conductive ink on the segment part. The sensor array is robust, simple, very low cost, good resolution, and highly volume efficient. The 16 sensors merely occupy the already available volume above the cantilever sections of the segments. This innovation offers very high levels of design synergy and is absolutely key to realizing a practical low cost real world haptic device.

In some embodiments, the micro-controller to apply autoscaling to the sensor data allows one lover to provide signals and the other lover to scale the sensations at the other end. Genital "fit" becomes a variable one can control in this haptic sex toy world thanks to the application of a biomimetic sensor array and intelligent embedded software.

The actuators, sensors, and other features described with respect to FIGS. 20A-20C can be used for sex toys, male and female. They can also be used as part of a simple touch surface allowing two hands to communicate.

Figure 21B:
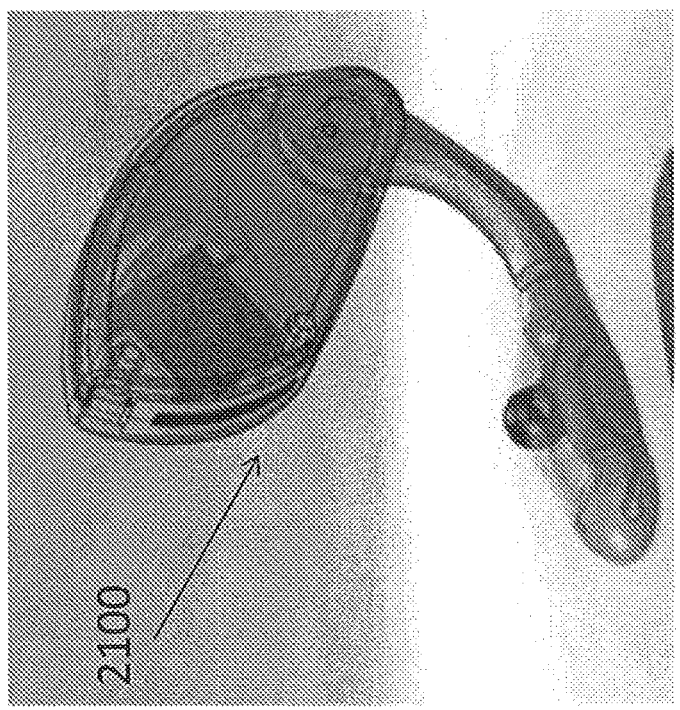
FIGS. 21A-21B show another exemplary embodiment of a sexual stimulation device or massager.
Figure 21A:
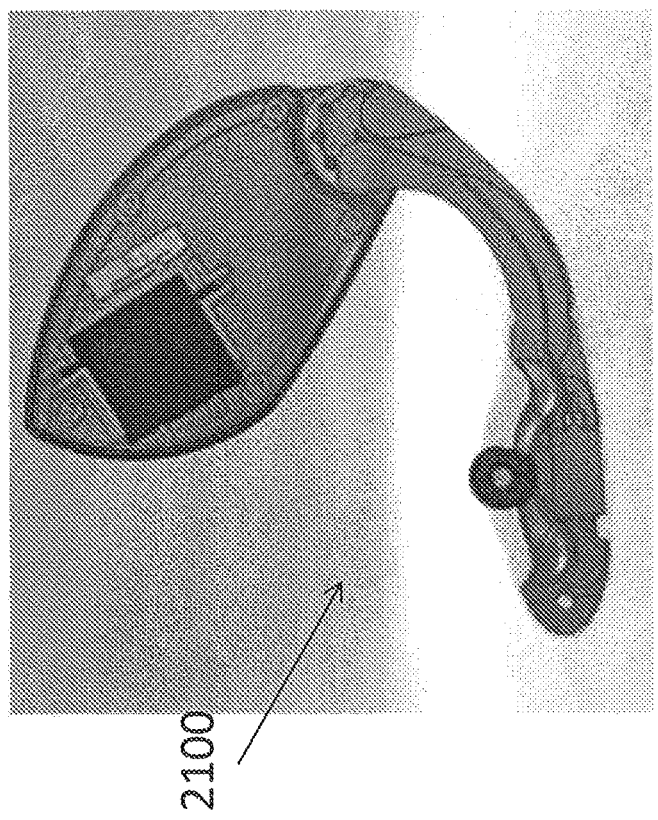

Referring to FIGS. 21A-21B, a massage device 2100 includes a handle portion and a distal portion, distal portion incorporating one or more moveable massage elements. The total volume, girth, and dimensions of the device can be chosen such that the assembly can be comfortably inserted into a human females vaginal canal for stimulation of internal structures, i.e. G spot, or for insertion into anal canal and/or for insertion in human male anal canal for prostate stimulation.

The massage elements can be substantially constrained to a 2 dimensional or 3-dimensional path. The massage elements can move relative to both handle and distal portion. The massage elements' motion can be defined by mechanism in distal portion, or handle portion, or combination of distal and handle portion. The massage element scan be capable of transmitting or generating vibratactile stimulation while in motion along said path. The massage elements can move under an elastic membrane. The massage elements can exert substantial forces against body surfaces while in motion. The massage elements can be manually controlled by an rotatable or translatable mechanism in the handle portion or by electromechanical assembly in handle portion.

The handle portion and distal portion may be coupled by flexible cable containing force transmissive elements and or electronic transmission elements, i.e., the handle portion is a remote control allowing distal portion to be inserted in body while handle portion is manipulated by oneself or a partner.

The massage elements' positions can be controlled by tension cables. A cable can pull each massage element against a spring located in distal portion. The cables can be disposed on opposing sides of a massage element, allowing pull-pull forces. The cables can be arranged in a pull-pull configuration connected to a rotatable capstan. The capstan can be responsive to electromagnetic actuator torque of force. The capstan can be responsive to self-contained servo actuator with internal position control, thus capstan rotation angle and resultant massage element(s) position are determined by open loop control signal provide to servo actuator. The capstan can be driven by motor and gear train without internal position sensor for servo actuation angle. The capstan drive mechanism can be combined with a sensor in the distal end responsive to position of massage element(s).

The sensor information can be used to close the loop on massage element(s) position relative to distal and or handle end. Each massage element's position can be controlled by user input, i.e. pressure sensing resistor or capacitive sensor incorporated into handle portion. The position control can be comprised of an electronic position control circuit active in maintaining the position of the massage element(s) relative to the input control signal from the position sensor responsive to the user input. The sensor control scheme can include employing a sensor connected to a microcontroller actively servo controlling position of massage element(s) in response to one or more position sensors.

The massage element(s) can be controlled in 2-D or 3-D path control. Tension cables can be arranged on linear actuator such that one cable is tensioned and translated relative to distal and or handle end while opposing cable experiences opposite translation, thus total cable length is substantially constant.

The distal portion and handle portion of device can share a rotatable joint as an adjustment. The distal portion and handle portion of device can share a translation degree of freedom as an adjustment.

The distal portion of massage element can have one or more features intended to permit one section of the distal portion to be deformed and or displaced with respect to the other portion, which may be achieved with one or more cuts or areas with removal of material. The bisected distal portion can include a degree of intentional freedom of motion in one or more preferred directions in combination with an electromechanical actuator responsive to electrical signals intended to displace degree of freedom in response to electrical signal.

A DC motor can be used to turn torque into a force between two or more sections of bisected distal end portion. A cam can act in a slot incorporated into one section of the distal portion where the motor is substantially attached to the other section of the distal portion, torque from DC motor creating a resulting force between slot and motor body, thus forcing bisected sections of distal portion in one or more directions or both. The DC motor or other electromechanical actuator, i.e. solenoid, constant force solenoid, voice coil, etc, can be driven by an amplifier circuit to provide single ended or bipolar electrical excitation of the actuator, thus providing transduction of any range of DC to AC signals to the mechanical assembly. The amplifier and motor arrangement can be responsive to the superposition of DC and AC waveforms.

A moving massage element can include a magnetic material, i.e. high energy product magnetic material, and distal portion contains a coil of wire, magnetic material being forcefully responsive to magnetic field induced by coil excited by electronic circuit.

Tension on drive cables or reflected forces on drive mechanism can be sensed and given to electronic circuit or microcontroller, thus a representation of what the massage element is resisting can be conveyed to another device.

There can be a touch sensitive pad for the user to control the position of the massage ball. Further, the distal end incorporates a hinge/beam design allowing a DC motor with an eccentric arm to drive one half of the distal end relative to the other in a swelling and contracting motion with frequency response from DC to several hundred Hz. This actuator is both kinesthetic and vibratactile in nature.

Use of a worm gear on a rotating shaft where the worm advances and retracts the linear position of a carrier portion, which is threaded to receive the worm as a nut with female threads, and simultaneously the carrier portion provides a rotatable bearing for a finger portion that rides along with the carrier and has its own mating teeth that engage the worm gear. Functionally, as the worm is rotated, the finger portion rotates through a 180 degree arc as it also translates back and forth. This would be ideal for a very high force G or P spot massager. It may or may not be back-drivable.

An alternate concept for the distal end of this massager concept of FIGS. 21A-21B involves a 2-DOF gimbaled cable drive where the massager is driven by either servos or by the user manually via a proximal input surface. In the passive case, the massage tip is cable driven and connected to a 2-DOF input gimbal with a mechanical advantage.

Thus, a massage device as described herein can be configured to be inserted into vagina or anus. The device can include a distal (shaft) and handle portion. The handle portion may be rigidly attached to distal (shaft) portion. The handle portion may be associated by a flexible cable of a length allowing handle to be used as a remote control. The device can include a plurality of segments that move relative to each other and the handle portion while constrained by the handle portion. The device can include a plurality of segments that move relative to each other and are not constrained by the handle portion. The segment can move in a peristaltic fashion such that the device selectively contracts and expands portions in order to aide in insertion or even insert on its own. The segments can move in a random fashion relative to each other or the handle portion. The segments can move in a pre-determined sequence. The segments can be controlled by actuators located in the distal portion. The segments can be controlled by one or more actuators located in handle portion. The segments can be actuated by cables in a pull-pull arrangement. The segments can be actuated by cables acting against springs. The segments can be actuated by screw thread actuators intended to convert rotation into translation, i.e., ACME thread drive, where a single DC motor rotates single drive shaft. Switches or sensors in combination with an electronic circuit can alternate the motor's rotation direction to produce oscillating mechanical motion where segments move in a rhythmic pattern. The magnitude of rotation of motor and speed of rotation can be controllable by user. A plurality of segments can be arranged on a single drive shaft rotatably attached to a plurality of screw elements where each segment has a female thread and the shaft rotates all screw elements at once. Screw elements can be a combination of left-hand and right-hand threads such that rotation of the drive shaft in one direction produces opposing motion for segments with opposite thread hands. Screw direction may be alternated or an arbitrary arrangement. A segment can include an outer ring joined to a coaxial threaded element by an island of material. The shaft portion of the distal end can incorporate an open channel thus allowing passage of a plurality of segments. Segments being supported or aligned by interaction between annular groove in segment and shaft. Segments can incorporate individual strain sensing elements such that the circumferential pressure or deformation of a segment with deformable structure may be individually measured and processed by a microcontroller or other electronic circuit. The shaft portion can incorporate an accelerometer providing one or more axis acceleration information to microcontroller or electronic circuit. The position of segments can be determined by closed loop controller responsive to sensors in handle portion. The handle portion can include an array of pressure or position or proximity sensors in conjunction with a processing means to control segments in a correlated or random fashion.

In one embodiment, based on differential motion, a phallic device can include a series of differentially paired sections that move relative to each other. A single drive motor and electronics can be configured to alternate the rotation to create spreading and contracting segments. One motor can drive RH and LH threaded ACME thread sections that are alternately arranged to produce opposite motion for one input rotation.

In one embodiment, a folding finger actuator can be passive and include no electronics or actuators in the simplest embodiment. A single molded polypropylene part has built in living hinges permitting the distal end to be folded forcefully with a mechanical advantage in response to moving a proximal portion of the device. G and P spot massage would be enabled with this device. A single tension cable connects the movable distal portion and the proximal handle. The kinematics of the end effector can be designed to match those of a human finger allowing one to reach where one can't usually go. Adding a vibrating tip to the device provides added function. The input portion has a finger positioning feature as shown it the illustrations below.

In one embodiment, a living hinge actuator array includes actuators that are formed in a flat panel and then rolled into a shaft or a sleeve for male or female stimulator. A sheet of polypropylene material can be machined to liberate hinged portions which are responsive to SMA contraction.

The invention(s) described herein have applications beyond shared sexual experiences between users. Embodiments of this invention may be deployed as diagnostic medical devices, such as to measure anatomical variations in a population, e.g. penis size, vaginal stiffness or measure a pregnant woman's uterus dilation (instead of crude, loosely-calibrated "by feel" approaches common today). By leveraging the sensing and networking capabilities together, such diagnostic medical device embodiments can accumulate a broad base of readings on a population, by way of transmission to a central server.

The systems and devices described herein can be used to deliver therapies either under control of the patient or, again by leveraging its network capabilities, under control of a therapist, such as for sexually dysfunctional or pre-orgasmic women, incontinent men, or men with premature ejaculation.

Therapies can include, but are not limited to, programs designed by storing groups of sensor signals on the servers on our network, then analyzing such "crowd-sourced" data to suggest a) optimal actuator inputs or b) actuator control in response to real-time sensor signals from the patient/user.

Moreover, the devices described herein are not intended to limit the female device 100 for male use or the male device 400 for female use. Either device, or multiple instances of either device, may be used to make intimate contact with either a male or female user. For instance, the male device 400 may be used to make intimate contact in the anal region of either a male or a female user. Additionally, a second (or 3rd, etc.) person may be present in the room to establish intimate contact, between one or more devices, and the user.

Further, it is to be understood that any of the embodiments of devices described herein can be used in place of any other. For example, the devices described with respect to FIGS. 18A-21B can be paired, networked, or placed in communication with one another or with any embodiment described herein similar to as described with respect to the pairing of devices 100, 400.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for sexual stimulation comprising:
    a sleeve having a longitudinal axis extending from a proximal end of the sleeve to a distal end of the sleeve; and
    a ring configured to translate over the sleeve along the longitudinal axis, the ring further configured to change in diameter to vary an amount of constriction placed on the sleeve.

2. The device of claim 1, further comprising a first actuator and a second actuator, the first actuator configured to control the translation of the ring over the sleeve, and the second actuator configured to control the constriction of the ring.

3. The device of claim 2, further comprising a drive cable connected to the first actuator, the ring configured to translate along the drive cable.

4. The device of claim 2, further comprising a controller, the controller configured to control the first actuator.

5. The device of claim 4, wherein the controller is configured to control the translation of the ring based upon position input from a paired device.

6. The device of claim 1, wherein the ring is configured to have a diameter of approximately 40-80 mm when unconstricted around the sleeve and a diameter of approximately 10-40 mm when fully constricted around the sleeve.

7. The device of claim 1, further comprising a position sensor coupled to the ring, the position sensor configured to detect a position of the device relative to a user.

8. The device of claim 1, further comprising a user control configured to adjust constriction of the ring or a position of the ring along the sleeve.

9. The device of claim 1, wherein the ring includes a telescoping portion or a coiled portion to provide for the change in diameter.

10. The device of claim 1, wherein the sleeve includes an outer layer configured to engage with the ring, the outer surface having a coefficient of friction of less than 0.1.

11. A device for sexual stimulation comprising:
    an elongate body having a longitudinal axis extending from a proximal end of a sleeve to a distal end of the sleeve;
    an expandable ring configured to translate along the longitudinal axis, the expandable ring configured to change diameter to expand beyond a diameter of the elongate body.

12. The device of claim 11, further comprising a vibrating element positioned at an angle relative to the elongate body.

13. The device of claim 11, further comprising a controller, the controller configured to control the translation of the expandable ring.

14. The device of claim 11, further comprising a controller configured to control an inflation of the expandable ring.

15. The device of claim 11, further comprising a handle attached to the elongate body.

16. The device of claim 11, further comprising a position sensor coupled to the expandable ring, the position sensor configured to detect a position of the device relative to a user.

17. The device of claim 11, further comprising a pressure sensor configured to detect a pressure of the expandable ring.

18. The device of claim 11, wherein the elongate body includes a semi-rigid elongate shaft.

19. The device of claim 11, further wherein the sleeve extends over the elongate body, and wherein the expandable ring is configured to translate in a space between the elongate body and the sleeve.

20. The device of claim 11, wherein the expandable ring is configured to inflate to change diameter.

* * * * *